US009566346B2

(12) United States Patent
Kost et al.

(10) Patent No.: US 9,566,346 B2
(45) Date of Patent: Feb. 14, 2017

(54) POSITIVELY CHARGED POLYSACCHARIDES FOR RNA TRANSFECTION

(71) Applicants: B.G. NEGEV TECHNOLOGIES AND APPLICATIONS LTD., Beer Sheva (IL); RAMOT AT TEL-AVIV UNIVERSITY LTD., Tel Aviv (IL)

(72) Inventors: Joseph Kost, Omer (IL); Riki Goldbart, Lehavim (IL); Tamar Traitel, Beer Sheva (IL); Eliz Lewis Amar, Beer Sheva (IL); Rinat Lifshiz, Bnei Dror (IL); Dan Peer, Kiryat Ono (IL)

(73) Assignees: B.G. NEGEV TECHNOLOGIES AND APPLICATIONS LTD., Beer Sheva (IL); RAMOT AT TEL-AVIV UNIVERSITY LTD., Tel Aviv (IL)

( * ) Notice: Subject to any disclaimer, the term of this patent is extended or adjusted under 35 U.S.C. 154(b) by 0 days.

(21) Appl. No.: 14/765,790

(22) PCT Filed: Feb. 5, 2014

(86) PCT No.: PCT/IL2014/050126
§ 371 (c)(1),
(2) Date: Aug. 4, 2015

(87) PCT Pub. No.: WO2014/122648
PCT Pub. Date: Aug. 14, 2014

(65) Prior Publication Data
US 2015/0366979 A1    Dec. 24, 2015

Related U.S. Application Data

(60) Provisional application No. 61/761,014, filed on Feb. 5, 2013.

(51) Int. Cl.
*C07H 21/02* (2006.01)
*C07H 21/04* (2006.01)
*A61K 48/00* (2006.01)
*A61K 47/48* (2006.01)
*C12N 15/11* (2006.01)
*A61K 9/51* (2006.01)
*A61K 41/00* (2006.01)
*C12N 15/113* (2010.01)

(52) U.S. Cl.
CPC ......... *A61K 47/4823* (2013.01); *A61K 9/5161* (2013.01); *A61K 41/0047* (2013.01); *A61K 48/00* (2013.01); *C12N 15/111* (2013.01); *C12N 15/113* (2013.01); *C12N 2310/14* (2013.01); *C12N 2320/32* (2013.01)

(58) Field of Classification Search
CPC .... C12N 15/113; C12N 2310/11; A61K 48/00
See application file for complete search history.

(56) References Cited

U.S. PATENT DOCUMENTS

| 2009/0253616 A1* | 10/2009 | Keen | A61K 31/473 514/1.1 |
| 2011/0054012 A1* | 3/2011 | Place | A61K 48/0066 514/44 R |
| 2011/0111501 A1 | 5/2011 | Kubo et al. | |
| 2012/0258534 A1* | 10/2012 | Lieberman | C07K 14/46 435/375 |
| 2012/0328668 A1* | 12/2012 | MacLachlan | C12N 15/113 424/400 |

FOREIGN PATENT DOCUMENTS

| CN | 102 268 096 A | 12/2011 |
| CN | 102657880 A | 9/2012 |
| CN | 102408488 B | 7/2013 |

OTHER PUBLICATIONS

Azzam T., Eliyahu H., Makovitzki A., Linial M., Domb A.J., Hydrophobized dextran-spermine conjugate as potential vector for in vitro gene transfection. J. Control Release,96(2): pp. 309-323. (2004).
Lee M., Nah J.W., Kwon Y., Koh J.J., Ko K.S., Kim S.W., Water-soluble and low molecular weight chitosan-based plasmid DNA delivery. Pharm. Res. 18(4): pp. 427-431. (2001).
Mansouri S., Lavigne P., Corsi K., Benderdour M., Beaumont E., Fernandes J.C., Chitosan-DNA nanoparticles as non-viral vectors in gene therapy: strategies to improve transfection efficacy. Eur. J. Pharm. Biopharm. 57(1): pp. 1-8. (2004).
Sieradzki R., Traitel T., Goldbart R., Geresh S., Kost J., 2008, Development and characterization of quaternized starch as a carrier for gene therapy applications, PhD thesis.
Morten Østergaard Andersen, Kenneth Alan Howard and Jørgen Kjems, RNAi Using a Chitosan/siRNA Nanoparticle System: In Vitro and In Vivo Applications, Methods in Molecular Biology, vol. 555, pp. 77-86. (2009).
Holzerny et al: "Biophysical properties of chitosan/siRNA polyplexes: profiling th polymer/siRNA interactions and bioactivity" J Control Release. 157(2):pp. 297-304(.2012).
Liu et al; "Bioconjugated Nanoparticle for DNA Protection from Ultrasound Damage" Analytical Sciences vol. 21. pp. 193-195. (2005).
Roy, K, Ghosn, B and Kasturi, S.P. et al; "Enhancing Polysaccharide-Mediated Delivery of Nucleic Acids Through Functionalization with Secondary and Tertiary Amines" Current Topics in Medicinal Chemistry 8, pp. 331-340. (2008).
David V Schaffer et al; "Targeted synthetic gene delivery vectors" Current Opinion in Molecular Therapeutics 2. pp. 155-161. (2000).
Ira Yudovin-Farber et al "Quaternary Ammonium Polysaccharides for Gene Delivery" Bioconjugate Chem 16, pp. 1196-1203. (2005).

(Continued)

Primary Examiner — Amy Bowman
(74) Attorney, Agent, or Firm — Knobbe, Martens Olson & Bear LLP

(57) ABSTRACT

A complex includes RNA and a positively charged modified polysaccharide selected from starch, amylose, amylopectin, galactan, chitosan, or dextrin. The complex can be formed into a pharmaceutical composition. The complex can be used in methods for RNA transfection, gene therapy and treatment of a disease, disorder or condition. The positively charged modified polysaccharide can be used in connection with RNA transfection into cells.

12 Claims, 20 Drawing Sheets

(56) References Cited

OTHER PUBLICATIONS

International Search Report and Written Opinion dated May 22, 2014 for PCT/IL2014/050126.
Akin Akinc et al., "Exploring polyethylenimine-mediated DNA transfection and the proton sponge hypothesis," J. Gene Med 2005; 7:657-663.
Yunching Chen et al., "Multifunctional Nanoparticles Delivering Small Interfering RNA and Doxorubicin Overcome Drug Resistance in Cancer," The Journal of Biological Chemistry 2010; 285:22639-22650.
Ahra Cho et al., "Characterization of cationic dextrin prepared by ultra high pressure (UHP)-assisted cationization reaction," Carbohydrate Polymers 2013; 97:130-137.
V. Dehousse et al., "Comparison of chitosan/siRNA and trimethylchitosan/siRNA complexes behaviour in vitro," International Journal of Biological Macromolecules 2010; 46:342-349.
Kenneth A. Howard et al., "RNA Interference in Vitro and in Vivo Using a Chitosan/siRNA Nanoparticle System," Molecular Therapy 2006, 14:476-484.
Chantal Pichon et al., "Chemical vectors for gene delivery: uptake and intracellular trafficking," Current Opinion in Biotechnology 2010, 21:640-645.
Xu-Li Wang et al., "A multifunctional and reversibly polymerizable carrier for efficient siRNA delivery," Biomaterials 2008; 29:15-22.
G. Theerawanitchpan, et al., "Chitosan and its quaternized derivative as effective long dsRNA carriers targeting shrimp virus in Spodoptera frugiperda 9 cells," Journal of Biotechnology, vol. 160, 2012, pp. 97-104.
A. Sizovs, et al., "Carbohydrate Polymers for Nonviral Nucleic Acid Delivery," Top Curr Chem. 2010, vol. 296, pp. 131-190.
J.E. Zuckerman, et al., "Polycation-siRNA nanoparticles can disassemble at the kidney glomerular basement membrane," Proceedings of the National Academy of Sciences, Feb. 21, 2012, vol. 109, No. 8, pp. 3137-3142.
B. Ballarín-González, et al., "Polycation-based nanoparticle delivery of RNAi therapeutics: Adverse effects and solutions," Advanced Drug Delivery Reviews, vol. 64, No. 15, 2012, pp. 1717-1729.
The partial supplementary European search report dated Aug. 24, 2016 by European Patent Office in the corresponding European Patent Application No. 14748479.4—8 pages.

\* cited by examiner

Complexes- incubation time in serum (hr)

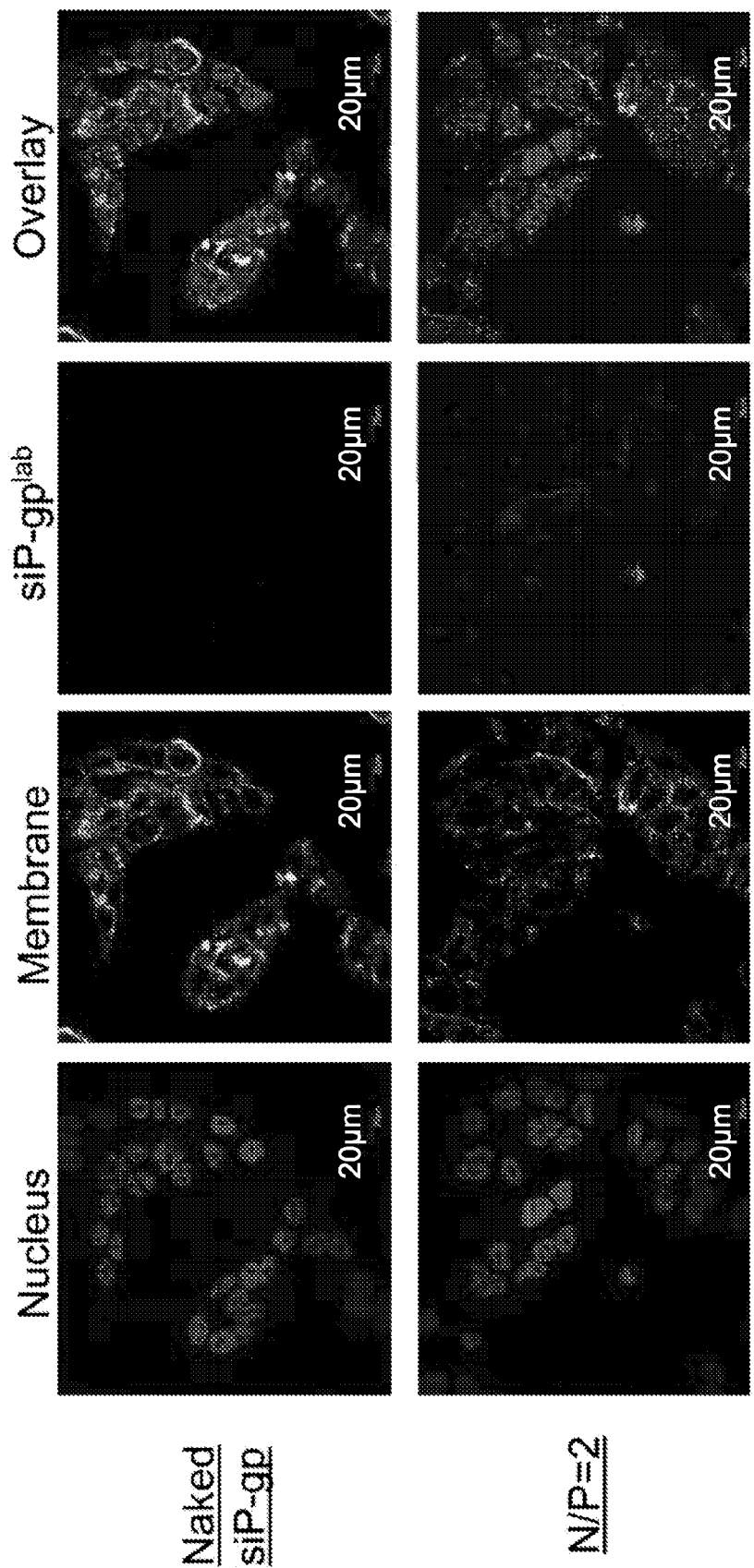

POSITIVELY CHARGED POLYSACCHARIDES FOR RNA TRANSFECTION

CROSS REFERENCE TO RELATED APPLICATIONS

This application is the U.S. National Phase of International Application No. PCT/IL2014/050126, filed Feb. 5, 2014, designating the U.S. and published in English as WO 2014/122648 on Aug. 14, 2014 which claims the benefit of U.S. Provisional Patent Application No. 61/761,014, filed Feb. 5, 2013.

FIELD OF THE INVENTION

The present invention relates to transfection of nucleic acids, particularly to transfection of RNA.

BACKGROUND OF THE INVENTION

Gene therapy involves using nucleic acid as a pharmaceutical agent to treat disease by introducing a target gene into cells and may become an effective treatment in cases where current treatments are insufficient. Recently, the RNA interference (RNAi) field has emerged as a new therapy approach. RNAi is a naturally occurring process of sequence-specific post transcriptional gene silencing, by which gene expression is inhibited RNAi offers tremendous therapeutic promise to silence genes that exhibit aberrant behavior and therefore cause disease. While the number of possible targets for this type of treatment is increasing, clinical success is still rare, due in part to imperfect delivery systems.

A major challenge in gene therapy is finding efficient ways to introduce the desired genes into target cells in a stable manner. Understanding the transfection process is essential in order to improve the efficiency of gene therapy. The transfection process includes introduction of a complex of carrier and nucleic acid which binds to the cell membrane, endocytotic cellular uptake of the complex by the plasma membrane, escape of the nucleic acid from the endosome (endosomal release) into the cell cytoplasm, and complex unpacking. In the case of DNA transfection, the process also includes a crucial step of transport to the nucleus and entrance of the DNA into the nucleus. In the case of RNA transfection, the rate-limiting steps appear to be the endosomal release and unpacking.

Non-viral gene delivery systems have become increasingly desirable in both, basic research and clinical settings as they eliminate some of the problems associated with viral vectors. Presently, non-viral carriers used for gene transfer consist mostly of liposomal formulations and synthetic cationic polymers. Non-viral gene delivery systems based on natural polysaccharides may be advantageous over the current available synthetic ones, due to several characteristics, such as biodegradability, biocompatibility, low immunogenicity and minimal cytotoxicity. However, in contrast with the abundance of structurally different synthetic polymers, there is only a small number of polycations of a natural origin available.

Several natural or modified cationic polysaccharides have previously been tested as carriers for DNA transfection. Azzam et al., 2004 tested dextran polysaccharide modified by grafting with mixtures of spermine and other natural/synthetic oligoamines of two to four amine groups, Lee et al., 2001 found that water-soluble low molecular weight chitosan is an efficient carrier for DNA delivery, and Mansouri et al., 2004 summarizes the use of chitosan as a carrier for DNA transfection.

In an earlier work (Sieradzki et al., 2008) the present inventors modified polysaccharides into cationic polysaccharides by the process of quaternization, which is the introduction of quaternary ammonium groups to the polysaccharide. The cationic polysaccharide has permanent or induced cationic charge and was shown to interact electrostatically with the negatively charged DNA to form complexes, thus condensing it effectively for delivery into cells.

SUMMARY OF THE INVENTION

It has been found in accordance with the present invention, that quaternized starch (Q-starch), is an efficient delivery vehicle for RNA transfection.

Thus, in one aspect, the invention is directed to a complex comprising RNA and a positively charged modified polysaccharide selected from starch, amylose, amylopectin, galactan, chitosan, or dextrin.

In another aspect, the invention is directed to the use of the complex of the invention in the process of transfection of RNA into cells.

In a further aspect the invention is directed to the use of a positively charged modified polysaccharide selected from starch, amylose, amylopectin, galactan, chitosan, or dextrin, in RNA transfection into cells.

In yet another aspect, the invention is directed to a pharmaceutical composition comprising RNA and a positively charged modified polysaccharide selected from starch, amylose, amylopectin, galactan, chitosan, or dextrin, and a pharmaceutically acceptable carrier.

In a still further aspect, the invention is directed to a method for RNA transfection into cells, comprising contacting said cells with a complex comprising a positively charged modified polysaccharide, said polysaccharide being selected from starch, amylose, amylopectin, galactan, chitosan, or dextrin, and RNA.

In another aspect, the invention is directed to a method for gene therapy of a subject in need thereof, comprising administering to said subject a complex of RNA and a positively charged modified polysaccharide, said polysaccharide being selected from starch, amylose, amylopectin, galactan, chitosan, or dextrin.

In a different aspect, the invention is directed to a method for treatment of a disease, disorder or condition selected from a tumor, asthma or psoriasis in a subject in need thereof, comprising administering to said subject a complex of RNA and a positively charged modified polysaccharide, said polysaccharide being selected from starch, amylose, amylopectin, galactan, chitosan, or dextrin.

BRIEF DESCRIPTION OF DRAWINGS

In FIGS. 1A-1C, The X axis is parts per million (ppm), the Y axis corresponds to peak intensity, and the numbers underneath the peaks correspond to the relative number of hydrogen atoms per the number of hydrogen atoms in other peaks. For example, in the quaternization reagent's NMR (FIG. 1A) there are 9 hydrogen atoms at the 3.1 ppm peak per 1 hydrogen atom at the 4.4 ppm peak. The lines above the peaks ("floating line") are integrals corresponding to the area under the peak, which represents the relative number of hydrogen atoms of the peak at a length unit, meaning that the length of the line of the peak at 3.1 ppm is 9 times larger that of the peak at 4.4 ppm.

FIGS. 8A-8B show cellular uptake of Q-starch/siP-gp$^{lab}$ complexes. Confocal microscopic images of NAR cells treated by Q-starch/siP-gp$^{lab}$ complexes (50 nM) are presented. A. Representative images of complexes at N/P=1 (upper panels) or N/P=2 (lower panels) after 1, 4, 8, and 24 hours of incubation with the complexes. The nucleus was stained with DAPI (blue), the membrane was stained with WGA Alexa Fluor® 555 (yellow), and siP-gp was labeled by DY677 dye (cy5 alternative, red). The right-most panel is after 24 hours at a higher magnification. B. Representative images via different channels (showing nucleus, membrane, siP-gp$^{lab}$ or an overlay of all three) after a 24 hours incubation with naked siP-gp (upper panels) or with complexes at N/P=2 (lower panels). Scale bar=20 µm except for zoom in images in which scale bar=5 µm.

DETAILED DESCRIPTION OF THE INVENTION

Figure 1A:
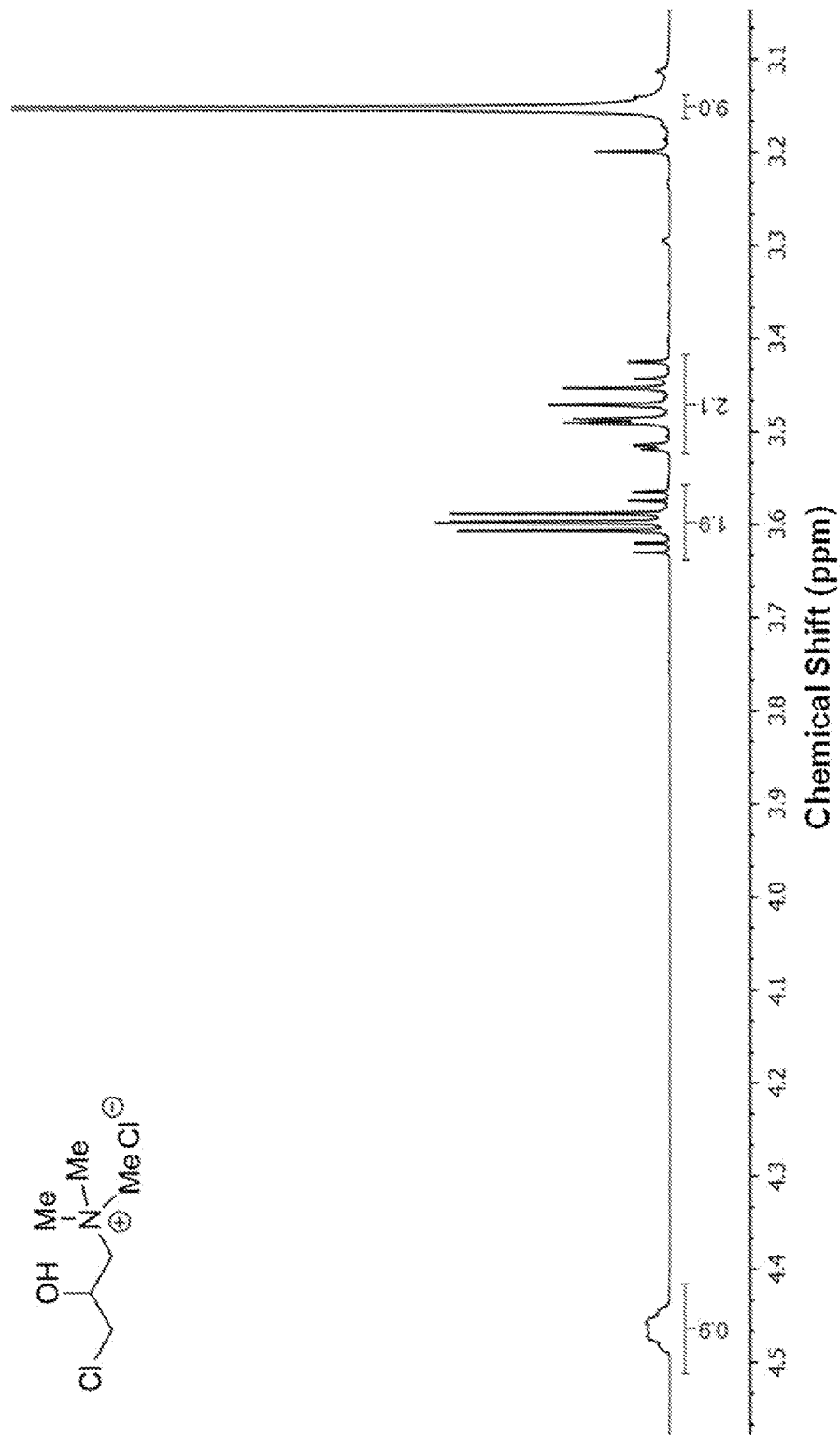
FIGS. 1A-1C show $H^1$NMR spectra of quaternized starch formed by the reaction described in FIG. 1D. (A) $H^1$NMR of pure 3-Chloro-2-hydroxypropyltrimethylammonium chloride (CHMAC, the quaternization reagent, depicted in the upper left corner). (B) $H^1$NMR of native potato starch (MW=26.5 kDa, depicted in the upper left corner), DMSO: dimethyl sulfoxide (C) $H^1$NMR of quaternized potato starch (Q-starch, depicted in the upper left corner) (D) Schematic illustration of the quaternization reaction depicting formation of quaternized starch repeating unit from starch and quaternizing agent. Rt: room temperature; DS: degree of substitution.

Transfection is the process of uptake of nucleic acids into cells. For condensation of a nucleic acid to a complex of appropriate size for cellular uptake during transfection, electrostatic interaction of a positively charged polymer with the negatively charged nucleic acid is needed. Consequently, for a polysaccharide to function as carrier for nucleic acid in gene delivery systems, unless it is naturally cationic, it has to be modified to a cationic polymer.

It has been found in accordance with the present invention, that transfection of RNA into mammalian cells is effectively facilitated by complexation with a positively charged polysaccharide.

Starch polysaccharide is composed of amylose (linear polymer) and amylopectin (branched polymer) with repetitive unites of glucose. The repeating units of amylose are linked by α(1-4) linkages, and the amylopectin consists of an α(1-4) linked backbone and α(1-6) linked branches. Dextrin is a group of low-molecular-weight carbohydrates produced by the hydrolysis of starch or glycogen, which is a multi-branched polysaccharide of glucose. Since starch is not cationic, it has to be modified in order to be an effective carrier for transfection.

Galactan is a polysaccharide made of galactose monomers, and is a component of pectin. Galactan also has to be modified to be cationic in order to be an effective carrier for transfection. It contains galactose chains which can serve as potential ligands for membrane receptor interaction. Since galactins (a family of galactose-binding lectin receptors) have altered levels in various cancers cells, they can provide a potential path for cancer gene silencing using modified pectic galactan (the part of pectin mainly comprising galactan), as a gene carrier.

Chitosan is a linear polysaccharide composed of randomly distributed β-(1-4)-linked D-glucosamine (deacetylated unit) and N-acetyl-D-glucosamine (acetylated unit). Because of the deacetylated amine groups, chitosan is positively charged at physiological pH and does not necessarily need to be modified to be an effective carrier for RNA transfection. However, since the positive charge of chitosan is pH dependent, it is advantageous to modify chitosan to have a permanent positive charge.

Additional glycosaminoglycans (GAGs) can be used with this invention as carriers for RNA transfection, for example chondroitin sulfate, dermatan sulfate, keratan sulfate, heparin, heparan sulfate and hyaluronan. All of these GAGs, except for hyaluronan, are sulfated and therefore have a negative charge. Therefore they should be modified in order be effective carrier for RNA Transfection It is appreciated that in order to be used in accordance with the invention, the polysaccharide must be positively charged at a physiological pH, which is between pH 7 and pH 8, either naturally or by being modified.

The present invention thus provides a complex comprising RNA and a positively charged modified polysaccharide, the polysaccharide being selected from starch, amylose, amylopectin, galactan, chitosan, or dextrin.

The term "modified" as used herein, refers to a polysaccharide which is substantially identical to the original polysaccharide but differing by the presence of at least a positively charged group, which can be introduced by various chemical modifications, such as esterification, etherification, oxidation, sialylation, fucosylation, sulphatation, methylation or acetylation. In the present invention, the polysaccharides were modified to become positively charged by a process of quaternization (Geresh et al., 2000).

Thus, in certain embodiments, the modified polysaccharide is a quaternized polysaccharide.

Quaternization is the process of introducing quaternary ammonium groups to a polysaccharide. Generally the hydroxyl groups of the polysaccharide are the site of incorporation of the ammonium groups, however, not all hydroxyl groups have the same likelihood of being modified in this method. For example, in the case of starch, the hydroxyl group at the 6' position of the glucose monomer is the most susceptible to quaternization.

Quaternization of polysaccharides can be performed by various methods, such as, e.g., those described in U.S. Pat. No. 4,031,307; Yudovin-Farber et al. (2005) Bioconjugate Chem 16:1196-1203; Houbin et al. (2004) Colloids and Surfaces A: Physiochem. Eng. Aspects 242:1-8; Huiqun et al. (2007) Carbohydrate Polymers 69:29-40; and Zhishen et al. (2001) Carbohydrate Research 333:1-6.

In certain embodiments, the polysaccharide is quaternized to its full capacity. For example, fully quaternized starch has at least 3.5-4% nitrogen per monomeric unit, by weight. This most likely corresponds to quaternization on the 6' position on the glucose in all monomers.

In certain embodiments, the polysaccharide is not quaternized to its full capacity.

The shape and size of the RNA-starch complexes are key factors in the transfection process. The molecular weight of the carrier and the molar ratio of positively charged amine groups on the polysaccharide to negatively charged phosphates on the RNA backbone (termed herein "N/P ratio") affect the shape and size of the complex, because the interaction between the positively charged polysaccharides and the negatively charged RNA causes the complex to condense into compact, ordered particles.

Thus, in certain embodiments, the molar ratio of positively charged amine groups on the positively charged polysaccharide and negatively charged phosphates on the RNA backbone, i.e. the N/P ratio, is in a range selected from about 0.1-100, about 1-5, or the ratio is about 2.

The term "about" as related to the molar ratio of positively charged amine groups and negatively charged phosphates (N/P ratio) means that N/P ratios that are 10% or less above or below the indicated values are also included.

The positively charged polysaccharides described above can be used as carriers for the transfection of various RNA species.

In certain embodiments, the RNA is single stranded RNA.

In certain embodiments, the RNA comprises a double stranded region of RNA (such as a hairpin structure), for example, a small interfering RNA (siRNA), short hairpin RNA (shRNA), or microRNA (miRNA), or long double stranded RNA (dsRNA), or antisense RNA (asRNA), or comprises a tertiary structure, such as a ribozyme. Such RNA can be used to silence genes via the RNA interference mechanism (RNAi).

Thus, in a certain embodiment, the RNA is siRNA, shRNA, miRNA or ribozyme. In certain embodiments, the RNA is an siRNA or a miRNA. In certain embodiments, the RNA is an siRNA. In certain embodiments, the RNA is a miRNA.

RNA interference (RNAi) is a process within living cells that moderates the activity of their genes. miRNA and siRNA, which are central to RNA interference, can bind to other specific messenger RNA (mRNA) molecules and either increase or decrease their activity, the latter, for example, by preventing an mRNA from producing a protein. RNA interference has an important role in defending cells against parasitic genes—viruses and transposons—but also in directing development as well as gene expression in general.

The term "siRNA" as used herein, refers to small interfering RNA which includes a sequence specific to a target mRNA. Such RNA is generally double stranded and of varying length, usually between 17 and 30 base pairs. siRNAs can include unpaired overhangs at the 5' and/or 3' ends and can form hairpin loop structures.

The term "microRNA" or "miRNA" as used herein, refers to a naturally found short RNA molecule, typically about 22 nucleotides long, having a sequence which is encoded by a genomic sequence and that can bind to a complementary sequence on a target mRNA transcript.

The term "ribozyme" as used herein, refers to an RNA molecule which is capable of performing a chemical reaction.

Starches, as well as amylose or amylopectin, from various sources can be used with this invention. The major sources of starch are the cereals (rice, wheat, and maize) and the root vegetables (potatoes and cassava). Other sources may include acorns, arrowroot, arracacha, bananas, barley, breadfruit, buckwheat, canna, colacasia, katakuri, kudzu, malanga, millet, oats, oca, polynesian arrowroot, sago, sorghum, sweet potatoes, rye, taro, chestnuts, water chestnuts and yams, and many kinds of beans, such as favas, lentils, mung beans, peas, and chickpeas.

Various types of starch can be modified and used as carriers in accordance with the present invention. For example, high molecular weight (MW) starches ($10^6$ Da) from potato, corn or rice, lower MW starches ($10^4$-$10^5$ Da), and very low MW starches ($10^3$ Da), which are obtained by cleavage, such as enzymatic cleavage or cleavage by ultrasound of the starch before or after quaternization. The starches from different plant sources may also differ in their amylose/amylopectin content.

Thus, in certain embodiments, the polysaccharide is starch. In certain embodiments, the starch is selected from rice starch, corn starch, potato starch, and potato soluble starch. In certain embodiments, the positively charged modified polysaccharide is quaternized starch.

Potato soluble starch used with this invention is produced by degradation of potato starch by enzymatic cleavage, and it contains 20-30% amylose and 70-80% amylopectin.

Other methods for generating soluble starch also exist, for example, mechanical chain scission using ultrasound.

In certain embodiments, the molecular weight of the starch is in a range selected from about $10^3$ to about $10^6$ daltons, about $10^4$ to about $10^5$ daltons, about $10^4$ to $5\times10^4$ daltons, or the molecular weight is about 26,500 daltons.

The term "about" as related to the molecular weight means that molecular weights that are 10% or less above or below the indicated values are also included.

Transfection efficiency greatly depends on polysaccharide size and cell type, and its rate appears to be limited by starch-RNA complex endosomal release and unpacking. Transfection efficiency can be improved by facilitating the release of the complex from the lysosome, i.e. by increasing the carrier lysosomotropic ability. The lysosomotropic ability may be increased by conjugating to the starch a lysosomotropic agent such as an amine of intermediate pK, e.g., imidazole or morpholine. The lysosomotropic agent can be grafted on a positively charged polysaccharide, e.g., a fully or partially quaternized starch.

In certain embodiments, the complex further comprises one or more lysosomotropic agent covalently attached to the polysaccharide.

In certain embodiments, the lysosomotropic agent is an imidazole group or derivative thereof.

Gene therapy refers to the introduction of genetic information into cells in order to treat disease. Often DNA encoding a functional gene is used to replace a mutated gene, but other forms of gene therapy exist, involving inserting a therapeutic protein drug or influencing the expression of endogenous genes, such as for example, by RNAi. Some obstacles to successful gene delivery include induction of an immune response, cytotoxicity to healthy cells, and difficulty in achieving an effective concentration of the drug at the site to be treated, and therefore it is advantageous to direct the drug to the target cells, thereby enabling more effective treatment with fewer side effects. This can be achieved, inter alia, by adding targeting moieties such as ligands to the delivery system to mediate binding and internalization by receptors on the surface of target cells.

This approach can be useful in diseases of specific organs, such as, for example human immunodeficiency virus (HIV) or severe combined immunodeficiency syndrome (SCID) which involve hematopoietic cells, cystic fibrosis, which mainly involves airway epithelia, diabetes, which involves pancreatic cells, and tumors. For example, mannose cross-linked to molecular conjugates was used to target gene delivery to mannose receptors expressed by macrophages, and specifically to deliver the gene encoding α1-antitrypsin specifically to pulmonary macrophages (reviewed in Schaffer and Lauffenburger, 2000).

Cancer therapy often involves potentially life-threatening side effects that are caused by the cytotoxicity of the therapeutic agents. In order for the agents to be selective to the target cells, they can be coupled to ligands such as antibodies or other molecules which can bind to antigens that are specific to or more abundantly expressed on the target cells. This allows for more specific delivery of drugs to the target cells.

Examples for ligands that can be used for targeting of the RNA-polysaccharide complex to cells or tissues of interest include, for example peptides containing RGD sequence for binding to specific integrin receptors, growth factor receptors ligands such as EGF and TGFα, or antibodies to tumor-associated antigens.

Additionally, non-targeting moieties may be used with the complexes of the invention, for example polyethylene glycol (PEG) for stabilization of the complex and protection from enzymatic degradation, nuclear localization signal (NLS) for directing the complexes to the nucleus, or mitochondrial localization signal (MLS).

Thus, in certain embodiments, the complex further comprises a targeting ligand or a non-targeting moiety.

In view of the above, the complex of the present invention may be useful in the transfection of RNA into cells and/or in gene therapy. Thus, in one aspect, the present invention further provides the use of the complex of the invention as defined herein above, in transfection of RNA into cells.

Various types of cells can be used with the invention. Non-limiting examples include plant cells, bacterial cells, and animal cells such as insect cells or mammalian cells. In certain embodiments, the cells are mammalian cells. In certain embodiments the cells are rodent cells. In certain embodiments the cells are human cells.

The transfected cells can be cells in culture or can be in a tissue. The cells can also be grown in a bioreactor for mass production. The transfected cells can be tumor cells.

In certain embodiments, the cells are skin cells.

The term "transfection," as used herein, refers to the uptake of nucleic acids by a host cell via any suitable method known in the art, such as methods disclosed in Graham et al., 1973; Sambrook et al. (1989) Molecular Cloning, a laboratory manual, Cold Spring Harbor Laboratories, New York, Davis et al. (1986) Basic Methods in Molecular Biology, Elsevier, particularly calcium phosphate co-precipitation, direct microinjection into cultured cells, ultrasound-mediated gene transfection, and electroporation.

In certain embodiments, the transfection is in vitro, for example, transfection into cells in culture or into cells in an isolated tissue. Such cells can be later introduced into an individual for use in treatment. In certain embodiments, the transfection is in vivo, for example, to directly treat a condition in an individual in need.

In certain embodiments, the complex of the invention is for use in controlling the expression level of a gene. In certain embodiments, the complex of the invention is for use in elevating the expression level of a gene. In certain embodiments the complex is for use in lowering the expression level of a gene, or for abolishing expression of a gene.

In certain embodiments, the complex of the invention is for use in gene therapy.

In certain embodiments, the complex of the invention is for use in gene therapy for treating any disease, disorder or condition that is amenable to treatment with siRNA or with miRNA.

For example, the complex of the invention can be used for treating any disease, disorder or condition treatable by RNAi-based drugs, such as those that are already in clinical trials, for example a solid tumor, pancreatic cancer, familial adenomatous polyposis, acute renal failure, amyloidosis, Cicatrix scar prevention, complications of kidney transplant, delayed graft function, hypercholesterolaemia, kidney injury, pachyonychia congenital, age-related macular degeneration, choroidal neovascularization, diabetic retinopathy, diabetic macular edema, dry-eye syndrome, non-arteritic anterior ischaemic ocular hypertension, ocular pain, open-angle glaucoma optic atrophy, optic neuropathy, or infection by Ebola virus, respiratory syncytial virus or Hepatitis B virus.

In certain embodiments, the complex of the invention is for use in the treatment of diseases or disorders affecting the skin. In certain embodiments, the complex of the invention is for use in the treatment of diseases or disorders which can be treated by transfection of the complex of the invention into skin cells.

In certain embodiments, the complex of the invention is for use in the treatment of psoriasis. In certain embodiments, psoriasis can be treated by silencing one of the genes Bcl-xL, IGF-1R or FGFR2 (Lerman et al., 2011, Xu et al., 2011).

In certain embodiments, the complex of the invention is for use in the treatment of asthma. In certain embodiments, asthma can be treated by silencing the gene Syk kinase.

In certain embodiments, the complex of the invention is for use in the treatment of a tumor.

The term "treating" or "treatment" as used herein includes alleviating, abrogating, substantially inhibiting, slowing, reducing or reversing the progression of a condition, substantially ameliorating or reducing clinical symptoms of a condition, substantially preventing the appearance of clinical symptoms of a condition, or complete cure of the disease. With regard to cancer, the term refers to preventing or delaying cancer recurrence, inhibiting tumor growth or causing death of cancer cells. Such treatment can also lead to regression of tumor growth, i.e., to decrease in size or complete regression of the tumor, and to elimination of metastases. The terms "tumor" and "cancer" are used interchangeably herein.

The term "tumor" as used herein refers to an abnormal mass of tissue, the growth of which exceeds and is uncoordinated with that of the normal tissues, and persists in the same excessive manner after cessation of the stimulus which evoked the change. Normal cells, if they propagate, do so in a controlled manner. This term also refers to metastases i.e. secondary cancerous growth formed by transmission of cancerous cells from a primary growth located elsewhere in the body.

Tumors which can be treated by the use of the complex of the invention include, for example, carcinomas of breast, colon, rectum, lung, oropharynx, hypopharynx, esophagus, stomach, pancreas, liver, gallbladder and bile ducts, small intestine, urinary tract such as kidney, bladder and urothelium, female genital tract such as cervix, uterus, ovaries, choriocarcinoma and gestational trophoblastic disease, male genital tract such as prostate, seminal vesicles, testes and germ cell tumors, endocrine glands such as the thyroid, adrenal, and pituitary glands, skin such as hemangiomas and melanomas; sarcomas such as those arising from bone and soft tissues as well as Kaposi's sarcoma; malignancies of the brain, eyes and meninges such as astrocytomas, gliomas, glioblastomas, retinoblastomas, neuromas, neuroblastomas, Schwannomas, and meningiomas; hematological malignancies such as leukemia, lymphoma and multiple myeloma.

Thus, in certain embodiments, the complex of the invention is for use in the treatment of a disease, disorder or condition selected from psoriasis, asthma or a tumor.

In certain embodiments, the complex of the invention may be used for treating additional diseases or disorders which can be treated by siRNA or by miRNA, e.g. diabetes, metabolic syndrome, obesity and alopecia.

In another aspect, the present invention provides a pharmaceutical composition comprising RNA and a positively charged modified polysaccharide, the polysaccharide being selected from starch, amylose, amylopectin, galactan, chitosan, or dextrin, and a pharmaceutically acceptable carrier.

Methodology and components for formulation of pharmaceutical compositions are well known and can be found, for example, in Remington's Pharmaceutical Sciences, Eighteenth Edition, A. R. Gennaro, Ed., Mack Publishing Co. Easton Pa., 1990. Pharmaceutical compositions for use in accordance with the present invention thus may be formulated in conventional manner using one or more physiologically acceptable carriers comprising excipients and auxiliaries, which facilitate processing of the active agents into preparations that can be used pharmaceutically. Proper formulation is dependent upon the route of administration chosen.

The term "pharmaceutically acceptable carrier" refers to a vehicle which delivers the active components to the intended target and which will not cause harm to humans or other recipient organisms. As used herein, "pharmaceutical" will be understood to encompass both human and veterinary pharmaceuticals. Useful carriers include, for example, water, acetone, ethanol, ethylene glycol, propylene glycol, butane-1,3-diol, isopropyl myristate, isopropyl palmitate, mineral oil and polymers composed of chemical substances like polyglycolic acid or polyhydroxybutyrate or natural polymers like collagen, fibrin or polysaccharides like chitosan and alginate. The carrier may be in any form appropriate to the mode of delivery, for example, solutions, colloidal dispersions, emulsions (oil-in-water or water-in-oil), suspensions, creams, lotions, gels, foams, mousses, sprays and the like.

The composition of the invention can be administered in a variety of ways. The routes of administration include, but are not limited to, intratumoral, intraliver, intradermal, transdermal (e.g. in slow release formulations), intramuscular, intraperitoneal, intravenous, intracoronary, subcutaneous, oral, epidural, intraocular, auricular (otic), intrauterine extraamniotic, vaginal, topical, and intranasal routes. The composition of the invention can be administered also as eyedrops or ear-drops. Any other therapeutically efficacious route of administration can be used.

For injection, the active ingredients of the compositions of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

For oral administration, the compositions can be formulated readily by combining with pharmaceutically acceptable carriers well known in the art. Such carriers enable the compositions of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

The compositions of the present invention may also be formulated in rectal compositions such as suppositories or retention enemas, using, e.g., conventional suppository bases such as cocoa butter or other glycerides.

The compositions of this invention can also be administered topically to a subject, e.g., by the direct laying on or spreading of the composition on the epidermal or epithelial tissue of the subject, or transdermally via a "patch". Such compositions include, for example, ointments, lotions, creams, solutions, gels and solids, with or without chemical enhancers, which are substances used for affecting penetration or permeation of drugs. Chemical penetration enhancers (CPEs) can increase permeability by acting as solvents dissolving lipids or denaturing skin proteins. In other cases, CPEs can modify drug solubility in the skin thus increasing drug penetration. Examples for CPEs include alcohols, amines and amides, urea, amino acids and their esters, fatty acids and their esters, macrocyclic compounds, sulfoxides, and tensides.

Pharmaceutical compositions suitable for use in context of the present invention include compositions wherein the active ingredients are contained in an amount effective to achieve the intended purpose. More specifically, a "therapeutically effective amount" means an amount of an active ingredient effective to prevent, alleviate or ameliorate symptoms of a disease or disorder or prolong the survival of the subject being treated.

Determination of a therapeutically effective amount is well within the capability of those skilled in the art, especially in light of the detailed disclosure provided herein.

Depending on the severity and responsiveness of the condition to be treated, dosing can be of a single or a plurality of administrations or a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

In yet another aspect, the present invention provides the use of a positively charged modified polysaccharide, the polysaccharide being selected from starch, amylose, amylopectin, galactan, chitosan, or dextrin in RNA transfection into cells.

In still other aspects, the present invention provides methods for RNA transfection into cells, comprising contacting the cells with a complex comprising RNA and a positively charged modified polysaccharide, the polysaccharide being selected from starch, amylose, amylopectin, galactan, chitosan, or dextrin.

The term "contacting" as used herein relates to physical contact of the complexes and the target cells. The contacting can be direct, i.e. directly applying the complexes to the target cells, such as when applying a solution of complexes to cells in culture or by topical administration to the skin when the target cells are skin cells of the outer layer, or it can be indirect, such as when applying the complexes to the outer layer of the skin when the target cells are keratinocytes in the basal layer, when applying the complexes to the blood stream by intravenous administration when the target cells are tumor cells of an internal organ, or in other uses when the complexes are not applied directly to the target cells, such as applying the complexes to a membrane, such as to the eardrum (tympanic membrane), amniotic sac, the eye, or by an intratumoral, subcutaneous or intramuscular injection.

In a further aspect, the present invention also provides a method for gene therapy of a subject in need thereof, comprising administering to the subject a complex of RNA and a positively charged modified polysaccharide, the polysaccharide being selected from starch, amylose, amylopectin, galactan, chitosan, or dextrin.

The complexes of the invention can further be used for genetic engineering of food, plants or other biological products, for fuel replacement, or as a metabolic engineering tool for bioreactor cell growth.

In yet another aspect, the present invention additionally provides a method for treatment of a disease, disorder or condition selected from a tumor, asthma or psoriasis in a subject in need thereof, comprising administering to the subject a complex of RNA and a positively charged modified polysaccharide selected from starch, amylose, amylopectin, galactan, chitosan, or dextrin.

In certain embodiments, the methods for RNA transfection, gene therapy and treatment of diseases or disorders also include the application of ultrasound to increase transfection efficiency. The ultrasound may be applied at different times relative to application of the complexes, depending on the method of application of the complexes of the invention, on the organ treated and on the desired effect of the ultrasound. For example, when the complexes are administered by an intratumoral injection, the ultrasound may be applied immediately after administration of the complexes; when the complexes are administered intravenously, the ultrasound may be applied a few hours after administration, for example, 24 hour after the intravenous injection; alternatively, when the complexes are administered intravenously, the ultrasound can be applied prior to administration; when the complexes are applied topically, the ultrasound may be applied before, during and/or after administration of the complexes.

Thus, in some embodiments, the methods of the invention further comprise applying ultrasound to the cells prior to, at the same time, and/or following contacting the cells with the complex. Alternatively, ultrasound is applied to the cells before, during and/or after the transfection process.

By "during the transfection process" is meant from the time of contacting the cells with the complex and until the time of entry of the complex into the cells. By "after the transfection process" is meant from the time of entry of the complex into the cells until the time of gene silencing.

When the ultrasound is applied before application of the complexes, it can be applied 24 hours, 12 hours, 2 hours, 60 minutes, 30 minutes, 10 minutes, or immediately before application of the complexes. In certain embodiments, the ultrasound is applied immediately before application of the complexes.

When the ultrasound is first applied after application of the complexes, it can be applied three days, two days, one day, 12 hours, 6 hours, 2 hours, 60 minutes, 30 minutes, 10 minutes, or immediately after application of the complexes. In some embodiments, the ultrasound application is stopped when gene silencing has been achieved. In certain embodiments, the ultrasound is applied 30 or 60 minutes after application of the complexes.

Different types of ultrasound instruments are available, including a low frequency ultrasound and a high-intensity focused ultrasound (HIFU). Generally, the low frequency ultrasound is more applicable for superficial applications, for example, cell in culture or topical application in live animals. In order to target deeper tissues and organs, for example, in animal and human applications, the high intensity focused ultrasound can be applied. This instrument can focus the waves to the site of interest, based on MRI imaging or based on calculations.

The acoustic intensity of the low frequency ultrasound can vary between 2 mW/cm$^2$ and 15 W/cm$^2$ and usually varies depending on the target cells, tissue or organ and the instrument used. In certain embodiments, the ultrasound instrument is configured to provide an acoustic intensity of 2.14 mW/cm$^2$. In certain embodiments, the ultrasound instrument is configured to provide an acoustic intensity of 8.2 W/cm$^2$.

In the HIFU instruments, the acoustic intensity is focused on the target point and can be between 1 W to 50 W.

The ultrasound may be applied for a duration of between 2 seconds and 30 minutes. In some embodiments, the ultrasound is applied for a duration of 2, 5, 10, 20 or 30 seconds. In some embodiments, the ultrasound is applied for a duration of 1, 2, 5, 10, 20 or 30 minutes.

In some embodiments, for transfection into cultured cells, the ultrasound may be applied for between 2 and 30 seconds at an acoustic intensity of 2.14 mW/cm$^2$. In some embodiments, the ultrasound is applied for 5, 10 or 20 seconds at an acoustic intensity of 2.14 mW/cm$^2$.

In some embodiments, for transfection into tissues, the ultrasound may be applied for between 5 seconds and 30 minutes at an acoustic intensity of 8.2 W/cm$^2$. In some embodiments, the ultrasound is applied for 10 minutes at an acoustic intensity of 8.2 W/cm$^2$.

As found by the inventors (e.g., Example 14), the application of ultrasound may enhance various steps of the treatment, such as delivery of the complexes through skin layers or another tissue until reaching the target cells, entry into the cells, endosomal escape, de-complexation, and transport in the cytoplasm. Thus, in some embodiments, the ultrasound may be applied more than once, at different times during treatment. In some embodiments, the ultrasound may be applied more than once after application of the complexes.

The second application of the ultrasound may be according to the same parameters as the first application, such as for the same duration or at the same intensity. Alternatively, the parameters of the second application, e.g. duration, or intensity, may be different from those of the first application. Additionally, if ultrasound is applied more than twice during treatment, the parameters of any of the following applications of the ultrasound may be the same as or different from those of the first application.

The invention will now be illustrated by the following non-limiting examples.

EXAMPLES

Experimental

Materials Used:

Soluble starch (101252) was purchased from Merck. Sodium hydroxide (S-0399), 3-Chloro-2hydroxypropyltrimethylammonium chloride (348287), Dialysis cellulose membrane (D9652), Phosphate buffered saline (PBS) (P4417), for TAE buffer preparation (prepared in our lab as ×50 stock solution), Triz base (T6791), Ethylenediaminetetraacetic acid (EDTA) pH 8 (E1644) and Thiazolyl Blue Tetra-zolium Bromide (MTT) (M2128) were purchased from Sigma-Aldrich Inc. Hydrochloric acid 32% (08460201), Acetone (01030521), Ethanol (05250502) were purchased from Bio-Lab. Loading buffer (G190A) was purchase from Promega. Non-targeting siRNA (control non-silencing, sense-5'-UGGUUUACAUGUCGACUAA-3', SEQ ID NO: 1) (Non-targeting siRNA #5, D-001210-05-50), siRNA targeting against the human gene ABCB1 which encodes for P-glycoprotein (sense-5'-GACCAUAAAUGUAAGGUUU-3', SEQ ID NO: 2) (D-003868-05-005) and the same siRNA fluorescently labeled by DY677 (cy5 alternative) (especially constructed for our lab) were purchased from Thermo Scientific. RPMI 1640 medium (01-104-1A), a 22-nucleotide long microRNA was purchased from Ambion, Fetal Bovine Serum (FBS) (04-121-1A), Trypsin Ethylenediaminetetraacetic acid (EDTA) (03-052-1B), L-glutamine (03-020-1B), Penicillin-streptomycin (03-031-1B) were purchased from Biological Industries Beit Haemek. Lipofectamine 2000® (11668-027), Wheat germ agglutinin Alexa Fluor 555 conjugate (W32464) and Prolong gold antifade reagent with DAPI (P36935) were purchased from Invitrogen. Antibodies were purchased from abcam: primary antibody-mouse monoclonal to P-glycoprotein (ab10333), secondary antibody-goat polyclonal secondary antibody to mouse IgG-H&L (FITC) (ab6785) and isotype control-mouse IgG2a [ICIGGaA] (ab91361).

Starch Quaternization:

Starch modification with quaternary amine groups to obtain quaternized starch (Q-starch) was carried out according to Geresh et al., 2000). Briefly, 500 mg of soluble potato starch (hydrolyzed potato starch, Mw 26,765 Da, Sieradzki et al., 2008) were dissolved in sodium hydroxide solution (0.19 g/ml) to obtain 50 mg/ml starch concentration. The solution was then stirred continuously for 30 min at room temperature. 9 g (7.8 ml) of the quaternization reagent, 3-Chloro-2hydroxypropyltrimethylammonium chloride (CHMAC), were dissolved in distilled water (DW) (0.45 g/ml) and added to the starch solution. The reaction volume was continuously stirred for 20 h at room temperature. One volume of product was precipitated by adding 4 volumes of acidified (1% HCl) mixture of ethanol and acetone (1:3% vol.). The precipitate was washed 4 times with 25 ml of ethanol 80%, dissolved in a small volume (1-2 mL) of DW and poured into a 11 kDa cutoff dialysis bag that was placed in a vessel containing 5 L of DW. The water was replaced 4 times with fresh DW during 48 hr of dialysis. The dialyzed product was then dried by lyophilization.

Chemical Analysis of Quaternized Starch:

Quaternization of the starch was confirmed by $^1$H NMR spectroscopy with a 500 MHz Brucker spectrometer. NMR of the quaternization reagent and quaternized starch was done in $D_2O$ solvent and NMR of native starch was done in DMSO solvent. The nitrogen content (% N weight) of Q-starch was measured by the Kjeldahl method (Vogel, A. I., A textbook of quantitative inorganic analysis, Longman, London, 1961, pp. 256-257).

RNA:

for siRNA experiments, the non-targeting negative control siRNA sequence was UGGUUUACAUGUCGACUAA (SEQ ID NO: 1), the sequence of si-P-gp used for targeting the gene ABCB1 was GACCAUAAAUGUAAGGUUU (SEQ ID NO: 2). For microRNA experiment, a 22 nucleotide long miRNA was used.

Q-Starch/siRNA Complex's Preparation:

Complexes of Q-starch and siRNA were prepared at various N/P molar ratios (molar ratio between positive nitrogen groups on Q-starch and negative phosphate groups on siRNA backbone). Q-starch dissolved in double distilled water (DDW) (0.4 mg/mL) was added in aliquots, to solutions containing siRNA (amounts determined by the desired N/P ratio). Following gentle vortexing, the samples were incubated at room temperature for 40 min before use for complex formation through self-assembly.

Complex stability in human serum was evaluated using gel electrophoresis as described at Schiffelers, 2004, Nucleic Acids Research 32:e149. Briefly, samples of siRNA alone or complexed with Q-starch at N/P=2 were mixed with fresh human serum to give 50% (% vol) serum concentration and incubated at 37° C. The serum was donated by three unrelated volunteers from the lab, and three sources were used due to innate differences in serum activity between sources. At each time interval (0, 0.5, 1, 3, 4, 8 and 24 h) the samples were removed and stored at −20° C. until agarose (3%) gel electrophoresis was executed. Naked uncomplexed siRNA under the electrophoresis conditions would run along the gel and would be visible after staining with ethidium bromide. Complexes will remain visible in the wells.

Agarose Gel Electrophoresis:

For gel preparation, 3 gr of agarose powder were dissolved in 100 mL of ×1 TAE buffer solution (composed of 40 mM Tris-acetate and 1 mM EDTA, pH 8.0) and stained with ethidium bromide (0.2 μg/ml). The solution was warmed and poured into an electrophoresis tray with a plastic comb to form the loading wells. The gel was left to solidify for 30 min, after which it was placed in a horizontal electrophoresis apparatus (Wide Mini-Sub cell GT, BioRad) containing ×1 TAE buffer solution. Samples containing 0.5 μg siRNA, either alone or complexed with Q-starch at a desired N/P ratio, were mixed with ×6 loading buffer and loaded (15 μL) onto to the agarose gel (3% w/v). The gel was exposed to an electric field (160V) for 40 min, and then visualized by UV illumination (Visible and Ultraviolet Transilluminator, DNR Bio-Imaging Systems).

Complexes Characterization:

The Q-starch/siRNA and Q-starch/miRNA complexes were characterized using the methods below. For complex characterization non-targeting siRNA was used.

Atomic Force Microscopy (AFM):

Complex size and geometry were visualized by atomic force microscope. Before imaging, 5 μL of each sample was dispensed onto individual freshly cleaved mica surface, incubated at room temperature for 20 minutes, and dried with nitrogen gas. AFM measurements were performed at ambient conditions at room temperature using a Digital Instrument Dimension 3100 mounted on an active anti-vibration table. A 100 μm scanner was used (Microfabricated Si oxide NSC11\50 type Ultralsharp with integrated pyramidal). The 512×512 pixel images were taken in tapping mode with a scan size of up to 5 μm at a scan rate of 1 Hz.

Dynamic Light Scattering (DLS) & Zeta Potential:

The hydrodynamic size of the complexes was measured by dynamic light scattering (DLS). Spectra were collected by using CGS-3, (ALV, Langen, Germany). The laser power was 20 mW at the He—Ne laser line (632.8 nm). Correlograms were calculated by ALV/LSE 5003 correlator, which were collected at 90°, during 10 s for 20 times, at 25° C. The correlograms were fitted with version of the program CONTIN (provencher, 1982). Samples of complexes were each diluted to a final volume of 1 mL in DDW. Each sample was measured twice and solutions were further diluted until results were independent of dilution rate. Complexes' size is presented as average of triplicates. Samples from DLS were transferred to U-tube cuvette (DTS1060C, Malvern) for subsequent zeta potential measurements using Zetasizer (ZN-NanoSizer, Malvern, England). Each sample was measured at automatic mode, at 25° C. and the Smoluchowski model was used to calculate the zeta potential. For each sample the zeta potential value was presented as the average value of three runs, and the average value of each N/P ratio is presented as the average of triplicates. Samples from DLS were transferred to U-tube cuvette for subsequent zeta potential measurements using Zetasizer (Malvern). Each sample was measured three times and the average zeta potential was presented as average of triplicates.

Cell Culture of NAR Cell Line:

Ovarian cancer cell line NCI/ADR-RES (NAR) overexpressing the gene ABCB1, which encodes the protein P-glycoprotein (P-gp) were cultured in RPMI growth media containing 1% L-glutamine, 1% penicillin-streptomycin and 10% fetal bovine serum (FBS) at 37° C. and 5% $CO_2$.

Transfection and Biological Effect of Q-Starch/siRNA Complexes in Gene Silencing in NAR Cells:

NAR cells were seeded in a 6-well plate 24 hours before transfection in RPMI growth media at a density of $1.5*10^5$ cells/well. On the day of transfection, the culture media was removed, the cells were washed once with PBS and 800 μL of serum and antibiotic free media were added to each well. Q-starch/siRNA complexes, either with non-targeting siRNA or with siRNA targeting P-gp (siP-gp), were prepared at various N/P ratios as described above to reach 50 nM siRNA concentration in each well. Lipofectamine 2000® was used as a positive control carrier and prepared according to manufacturer's procedure. Untreated cells (negative control) were supplemented with serum and antibiotic free media (200 μL). The transfection complexes (200 μL) were added to the cells and incubated at 37° C. and 5% $CO_2$. For cells not treated by ultrasound, after 4 hours, 500 μL of growth media containing 30% serum and without antibiotics were added and further incubation was continued (24 or 72 hr) until FACS analysis was conducted.

Treatment with Ultrasound (US)

30 (for NAR cells) or 60 (for keratinocytes) min after adding complexes the cells were placed on top of a foamed polyethylene layer in an ultrasonic 13 cm plate horn (20 kHz Misonix-ultrasonic liquid processor S4000-010, max intensity 600 W) filled with 4 cm water. Ultrasound was applied for 5, 10 or 20 seconds at an ultrasound configuration of 1% amplitude and at a continuous mode. This configuration results in 2.14 $mW/cm^2$ acoustic intensity. After applying ultrasound the cells were removed to the incubator and after 4 hr of incubation, 500 μL of growth media containing 30% serum and without antibiotics were added. Further incubation was continued (24 or 72 hr) until FACS analysis was conducted.

Flow Cytometry Analysis:

Gene silencing efficiency was quantified by labeling the protein P-gp with a fluorescent antibody and then fluorescence activated cell sorter (FACS) analysis was performed. Following transfection (after 24 or 72 hr of incubation) the medium was aspirated from the wells, and cells were washed once with PBS, trypsinized and pelleted by centrifugation for 5 min at 250 g and 25° C. in 5 mL tubes. Each tube was re-suspended in FACS buffer (1% FBS in PBS) and divided into three FACS tubes. The first was non-labeled cells (the cells weren't treated with antibodies). The second was cells labeled with primary (I') antibody (mouse monoclonal specifically attaches to P-glycoprotein), and secondary (II') antibody (fluorescently labeled by FITC, which specifically attaches to the primary antibody). The third tube was cells incubated with secondary (II') and isotype (control) antibodies, for detecting non-specific attachment of antibodies to the cells. Each treatment with antibody was done as follows: The cells were centrifuged for 5 min at 250 g and 4° C. The cell pellet was incubated under ice for 30 min with 50 μL each antibody. For the second tube the cells were first incubated with the I' antibody (5 μg/mL) and then with the II' antibody (5 μg/mL). For the third tube the cells were incubated with a mix of both the II' (5 μg/mL) and isotype (1 μg/mL) antibodies. Following incubation the cells were pelleted and re-suspended in 450 μL of FACS buffer. Gene silencing was measured by flow cytometry using FACS caliber instrument (BD) equipped with a 488 nm Argon laser and a 530/30 band pass filter and the data analysis was done with BD Cellquest Pro™ software version 5.1.1. Percentage of gene expression was calculated by reducing the autofluorescence of the non-labeled cells from the fluorescence of the labeled cells and dividing by the fluorescence of the negative control untreated cells. Untreated cells were considered as 100% of gene expression.

Cell Viability:

Cell viability was assessed for the toxic effect of Q-starch/siRNA complexes and exposure to ultrasound separately using MTT assay.

For measuring the effect of ultrasound on cell viability, NAR cells were seeded in a 6-well plate 24 hours before transfection in RPMI growth media at a density of $2.5*10^5$ cells/well. The next day the culture media was removed, the cells were washed once with PBS and 2 mL of RPMI starvation medium (containing 1% L-glutamine, 1% penicillin-streptomycin and 5% FBS) were added to each well. Each cell plate was placed on top of a foamed polyethylene layer (as described above) in an ultrasonic 13 cm plate horn (20 kHz Misonix-ultrasonic liquid processor S4000-010, max intensity 600 W) filled with 4 cm of water. Ultrasound was applied for 5, 10 and 20 seconds at an ultrasound configuration of 1% amplitude and at a continuous mode. This configuration results in 2.14 $mW/cm^2$ acoustic intensity. After applying ultrasound the cells were removed to the incubator. Following 1 hr of incubation a standard MTT assay was performed according to manufacturer's procedure, as described below.

The toxic effect of Q-starch/siRNA complexes on NAR cells without ultrasound was evaluated by following the transfection procedure (as described above) with 20 nM siRNA concentration in each well. Following 72 hr of incubation a standard MTT assay was performed according to manufacturer's procedure.

Briefly, the cell media was replaced by 1 mL of fresh starvation media and 100 μL of MTT ((3-(4,5-Dimethylthiazol-2-yl)-2,5-diphenyltetrazolium bromide, a tetrazole)) solution (5 mg/mL in PBS) was added to each well. Cells were incubated for two hours in the incubator after which 1 mL of MTT solvent (acidified isopropanol 0.04M) were added to each well. The cell plates were incubated for additional 24 hours at room temperature in a sterile hood. The absorbance of each well was read at test wavelength of 570 nm and reference wavelength of 630 nm (the reference wavelength reading is used in order to compensate for various proteins in the culture medium which may affect the absorbance of the sample).

The percentage of viable cells after exposure to ultrasound was calculated as the ratio between the absorbance of treated cells and cells that were not exposed to ultrasound.

The percentage of viable cells after exposure to Q-starch/siRNA complexes was relative to the cells that were not treated with complexes.

Cellular Uptake of Q-Starch/siRNA Complexes in NAR Cells

Cellular uptake of Q-starch/siRNA complexes was visualized using a confocal microscope. NAR cells were seeded in a 12-well plate on an 18 mm glass coverslip 24 hours before transfection in RPMI growth media at a density of 1.2×105 cells/well. On the day of transfection the culture medium was removed, the cells were washed gently once with PBS, and 400 μL of serum- and antibiotic-free RPMI medium was added. Complexes were prepared as described above at N/P ratios of 1 and 2 using fluorescently labeled siP-gp (referred to as siP-gp$^{lab}$) to give Q-starch/siP-gp$^{lab}$ complexes at 250 nM (to reach 50 nM final concentration inside the well). The cells were supplemented by 100 μL of Q-starch/siP-gp$^{lab}$ complexes at N/P=1 or 2, and as a control by 100 μL of naked siP-gp$^{lab}$, after which the cells were incubated at 37° C. and 5% CO2 for 1, 4, 8, or 24 hours. At each time interval the cells were removed from the incubator washed twice with HBSS and fixed using with 4% paraformaldehyde. The cell membrane was labeled by WGA Alexa Fluor 555 conjugate (excitation 555 nm, emission 565 nm) according to the manufacturer's procedure. The cell coverslip was mounted by fluorescent mounting medium containing DAPI for nucleus staining (ProLong® Gold antifade reagent with DAPI). Confocal microscopy was performed on a FluoView 11 FV-1000 (Olympus) spectral confocal laser-scanning microscope using excitation of 405 nm, 559 nm, and 635 nm for DAPI, Alexa 555, and DY677 fluorophores, respectively. Images were processed using FV10-ASW 4.0 Viewer browser software and for each treatment the presented images represent the entire slide.

Porcine Skin Electrical Conductivity Measurements:

Ag/AgCl 4 mm disc electrodes were introduced into both diffusion cell compartments. Voltage of 100 mV AC at 10 Hz was applied using a function generator and the current measured with a Multimeter. Skin resistance was calculated using Ohm's law multiplied by the skin area to achieve skin resistivity (skin conductivity is the reciprocal of skin resistivity). Only intact skin samples with initial resistivity of 30 KΩ*cm$^2$ or higher were used.

Example 1

Chemical Analysis of Quaternized Starch

Figure 1B:
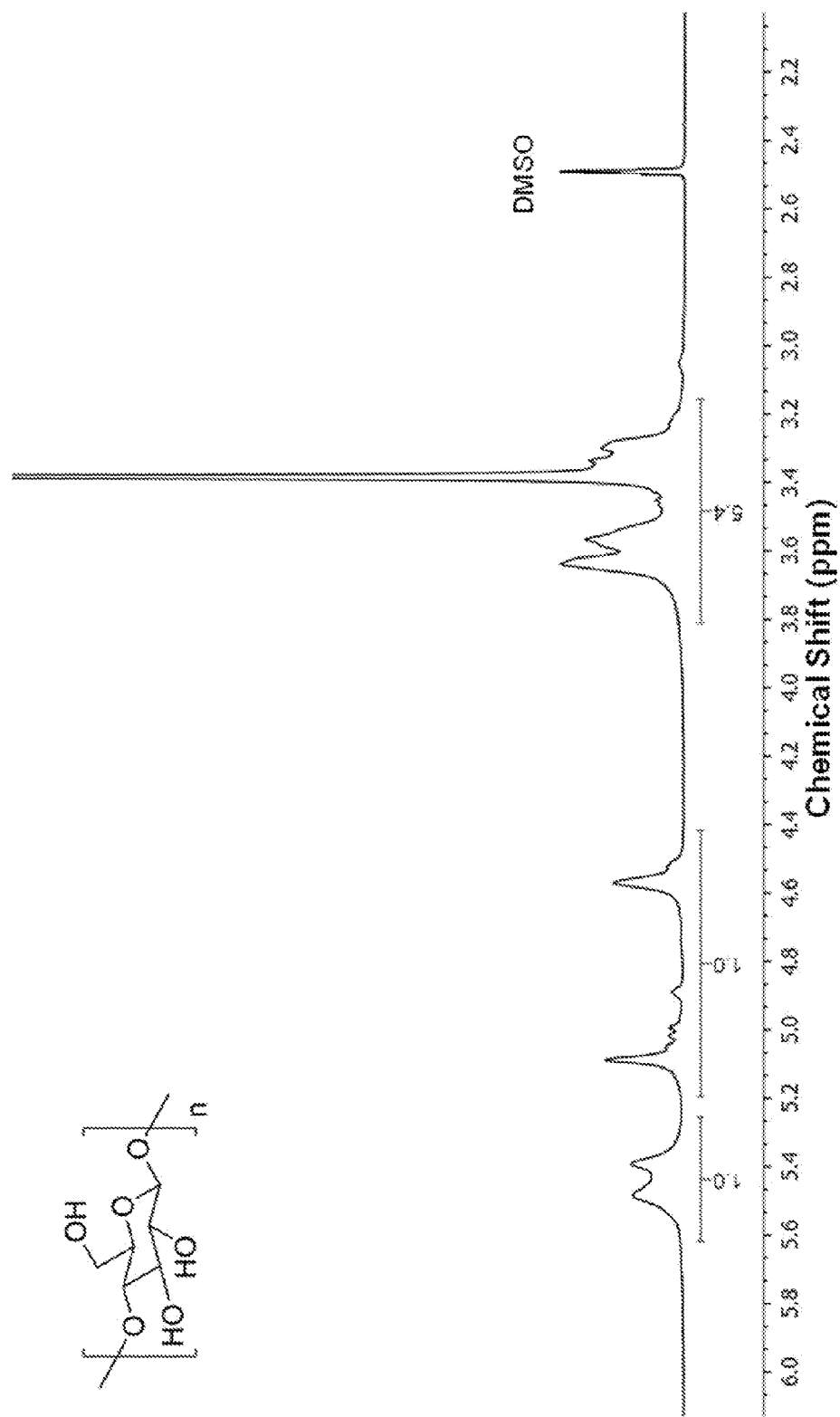
Figure 1C:
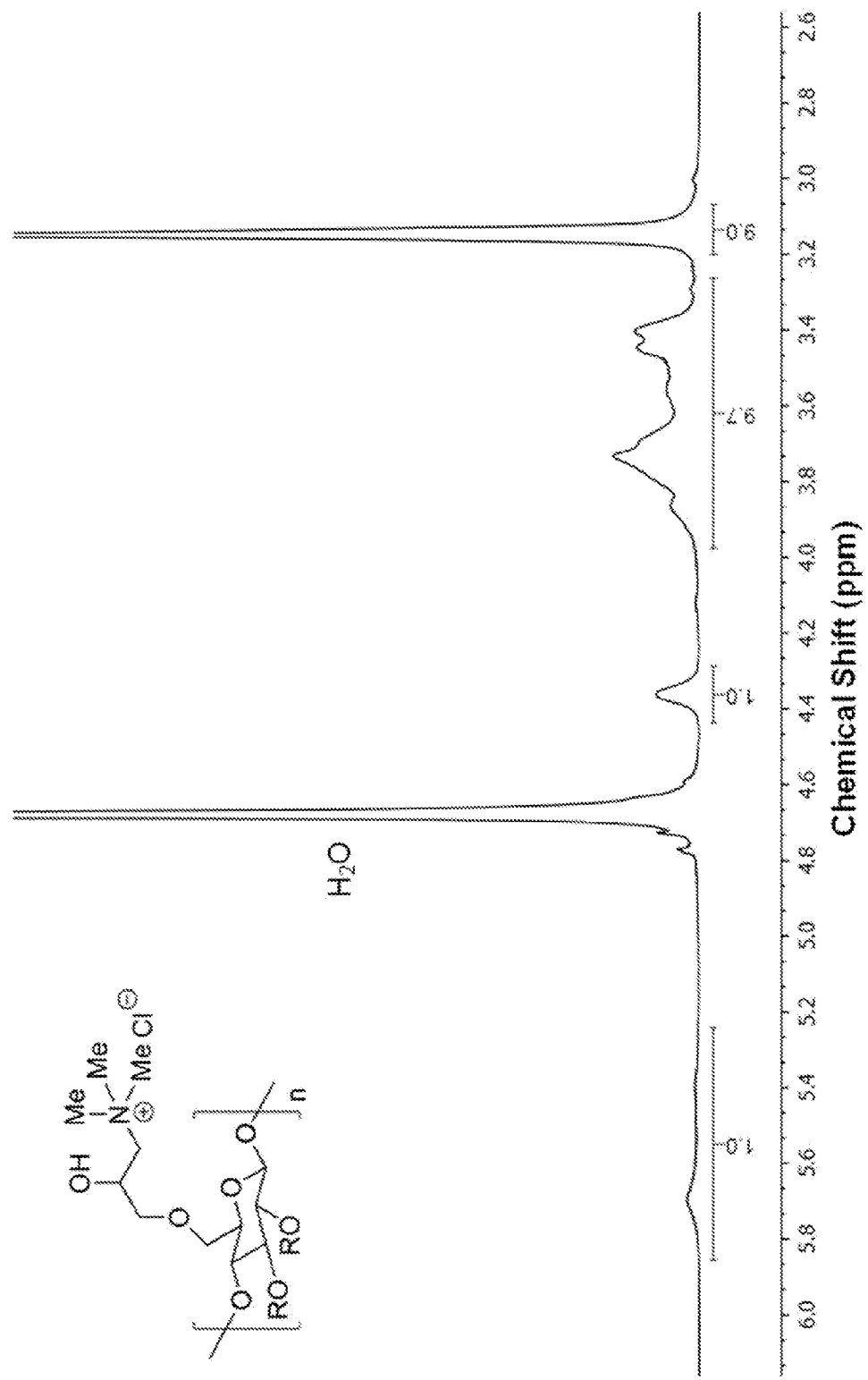
Figure 1D:
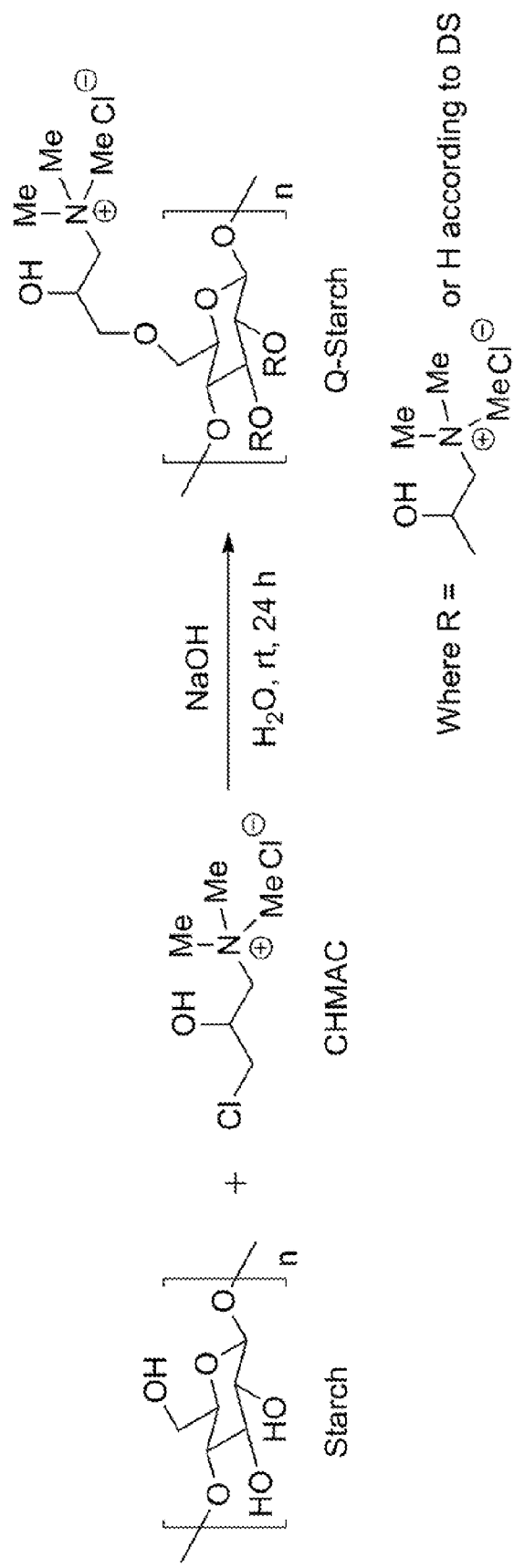

Starch modification is essential for the purpose of adding a positive charge to the starch polymer backbone. The introduction of the cationic group, CHMAC, into the polysaccharide was done as described at Geresh et al., 2000. Starch quaternization was confirmed by comparing the H$^1$NMR spectrum of the quaternization reagent (FIG. 1A), native starch (FIG. 1B) and modified starch (Q-starch, FIG. 1C). The peaks in each H$^1$NMR spectrum represent the hydrogen atoms in each of the tested molecules. The most significant peak that characterizes the reagent is the peak that appears at 3.1 ppm (FIG. 1A) which represents the 9 methyl hydrogens bound to the nitrogen atom of the reagent (FIG. 1D). As a result of the substitution of starch with the CHMAC moiety, this peak appears in the spectra of the modified starch (FIG. 1C) while absent in the spectra of the native starch (FIG. 1B). The peak at 3.4 ppm in FIG. 1B represents water contaminant hydrogens at the native starch sample that is typical to water contaminant in DMSO solvent. Nitrogen content of Q-Starch was found by the Kjeldahl method to be 3.5-4%. According to calculations based on quaternization of the 6' position in each glucose monomer of the starch, 4% is considered the maximum substitution. Therefore, the Kjeldhal and H$^1$NMR results of synthesized Q-starch confirmed starch.

Example 2

Q-Starch/siRNA Complex Formation

Figure 2:
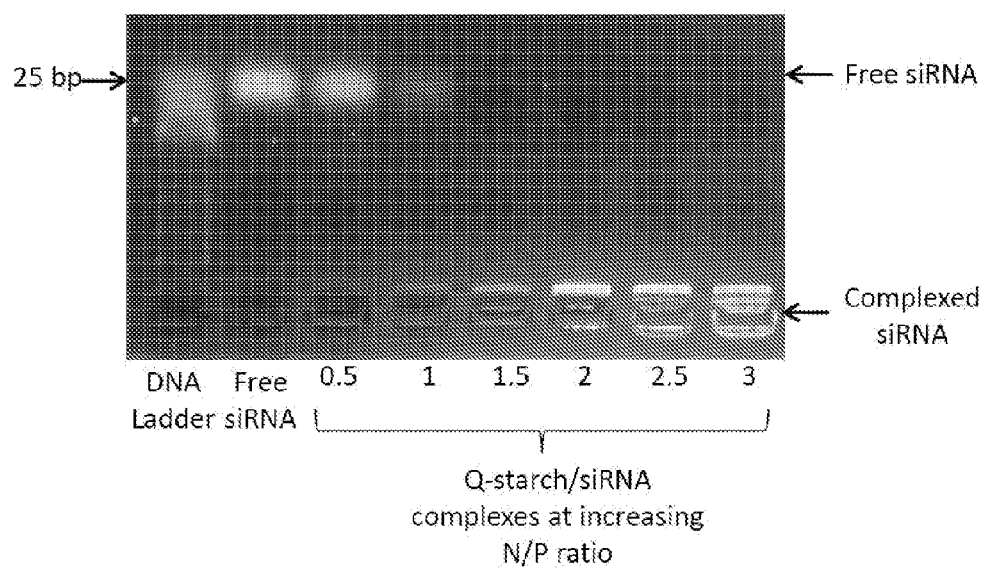
FIG. 2 shows Q-starch (quaternized starch)-siRNA complex formation by gel electrophoresis. Lanes: (left to right): DNA ladder, free siRNA (arrow pointing to the 25 bp ladder band), Q-starch-siRNA complexes at the indicated N/P ratios: 0.5, 1, 1.5, 2, 2.5 and 3. Free siRNA size is 19 bp and the complexed siRNA is seen around the wells.

Q-starch/siRNA complex formation is based on electrostatic interaction between positively charged Q-starch and negatively charged siRNA. The desired N/P ratio is the ratio in which Q-starch is able to form a condensed polyplex with siRNA and none of the siRNA remains free. Free siRNA at gel electrophoresis runs along the gel towards the positive electrode and can be visualized by the bright band that matches its size of 19 base pairs as determined by the DNA ladder. As N/P ratio increases, free fragments of siRNA are entrapped within the Q-starch/siRNA complexes and the free siRNA band gets less bright. The complexes are bigger in size than free siRNA and cannot run along the gel because of its agarose density. Therefore they can be seen inside the wells at the bottom of the gel and as N/P ratio increases the complex band gets brighter. As seen in FIG. 2, the minimal N/P ratio for full complexation was 2, because the complex band at the well is brightest and no free siRNA band is detected. At N/P ratio of 1.5, although the free siRNA band is too light to be detected, the complex band at the well is less bright than in N/P ratio of 2 and therefore the complexation is not full at this ratio.

Example 3

Q-Starch/siRNA Complex Characterization

Figure 3A:
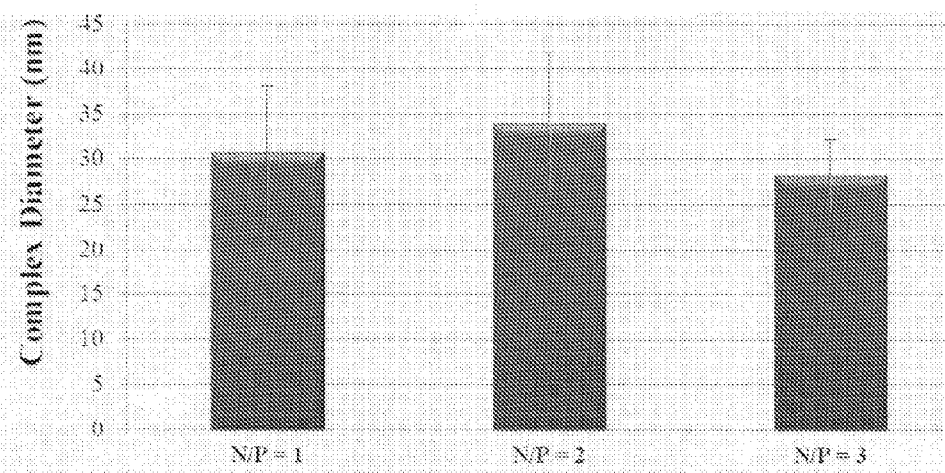
FIGS. 3A-3B show Q-starch-siRNA self-assembled nanoparticles at different N/P ratios. The bars correspond to N/P ratios of 1, 2 and 3, from left to right. (A) Mean particle diameter. (B) Mean zeta potential. The numbers represent an average of three preparations (n=3). The lines on each bar represent standard deviation.
Figure 3B:
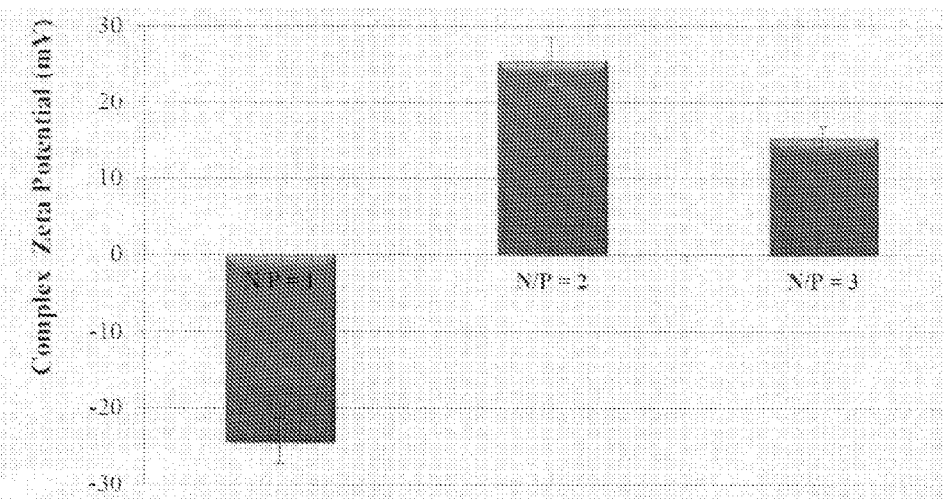
Figure 4A:
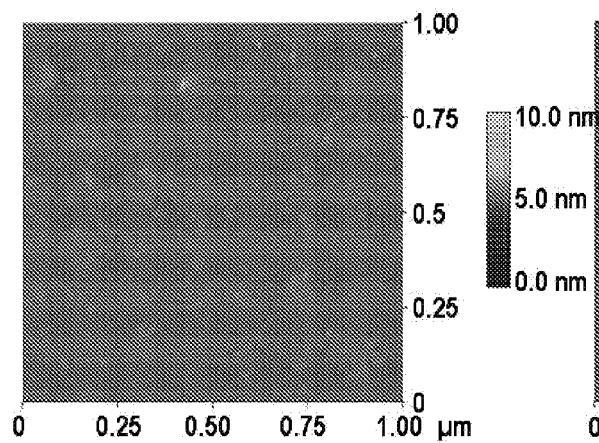
FIGS. 4A-4C show an atomic force microscope scan of particles. (A) Q-starch (7.5 ng/µl), (B) Q-starch-siRNA complexes at N/P=2 (250 nM siRNA and 7.5 ng/µl Q-starch) (C) free siRNA (250 nM).
Figure 4B:
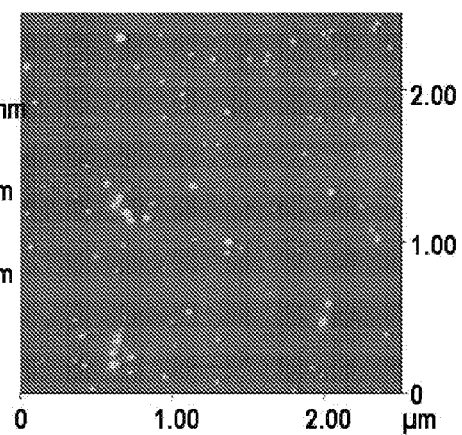
Figure 4C:
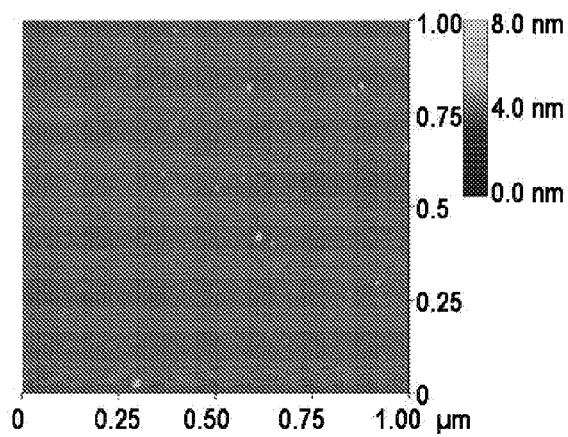

The diameter and charge of the siRNA/Q-starch polyplexes are shown in FIG. 3 for N/P ratios of 1, 2 and 3. As seen in FIG. 3A, the mean size of self-assembled Q-starch/siRNA complexes, as measured by Dynamic Light Scattering (DLS), was small and independent of the N/P ratio (between 28.3-34.0 nm in diameter). This is in contrast to polyplex formation with plasmid DNA and Q-starch (Sieradzki, 2008) (Mw ~26 kDa), in which the particle size was above 100 nm in diameter, as seen in Table 1 below, and decreased as the N/P ratio increased. In agreement with the gel electrophoresis results and as can be seen in FIG. 3B, at an N/P ratio of 1 the zeta potential is negative since free fragments of siRNA is still present in the polyplex solution, while above that ratio, the zeta potential turns positive. The relatively small complex size (diameter smaller than 100 nm) and positive charge of the siRNA polyplexes at N/P ratio of 2 and above indicate the capability of these complexes to enter cells through endocytosis. AFM scan confirmed the DLS results, as shown in FIG. 4. According to particle analysis by AFM, the mean size of complexes is in the range of 29.1-68.8 nm and the mean diameter is 44.4 nm.

Example 4

Comparative Results with DNA Complexes

TABLE 1

DNA Complex diameter according to DLS measurements.

| Carrier MW | N/P ratio | Complex diameter (nm) |
|---|---|---|
| 26,765 Da | 1.5 | 192.5 ± 23 |
| 26,765 Da | 3 | 108 ± 25 |

Based on data previously shown by inventors of the present application (Sieradzki, 2008), complexes with DNA (as presented in Table 1) are much larger than complexes with siRNA (as seen in FIG. 3A), and are condensed to a suitable transfection size (150-200 nm) only at N/P ratios of 3 and above. In general, increasing the N/P ratio for DNA complexes was shown to increase the number of nitrogen positive groups that are able to interact with the negative phosphate groups on the DNA backbone and condense the relatively large plasmid DNA to a smaller particle. However, based on the present results, complexes size show that the carrier does not have the same effect in the case of siRNA. As seen from FIG. 3A above, the size of siRNA/polycation complexes was independent of N/P ratio. The reason is that siRNA is already small (~13 nm) and unable to be condensed into a smaller size (Gary et al., 2007). It appears likely that in the case of siRNA, the carrier in fact helps it become large enough to be effectively be taken up by the cells and not be degraded.

Example 5

Complex Stability in Human Serum

Figure 5:
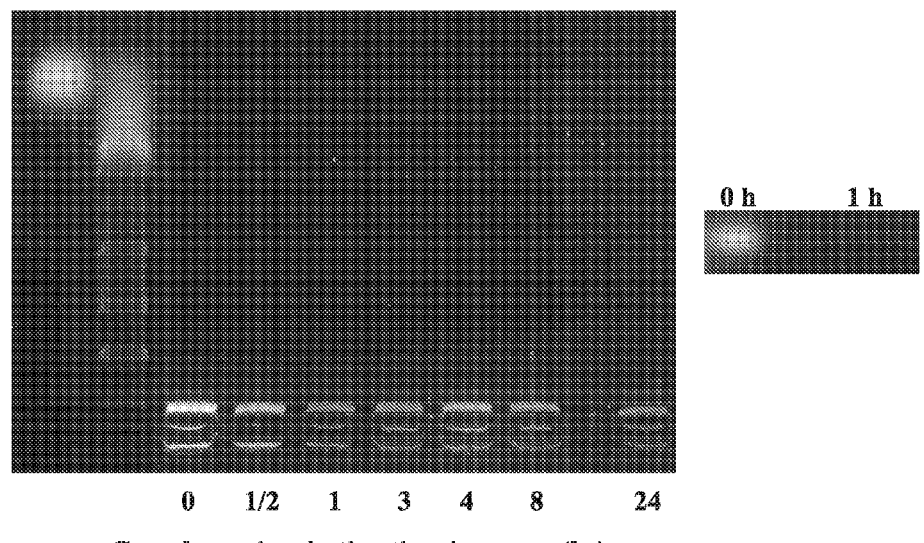
FIG. 5 shows degradation of polyplexes of siRNA/Q-Starch at N/P=2 by gel electrophoresis after incubation with human serum. The wells in the left panel correspond (from left to right) to naked siRNA (without incubation with serum), ladder, and incubation times of 0, 0.5, 1, 3, 4, 8 and 24 hours. The right panel shows naked siRNA not incubated with serum (left), and incubated with serum for 1 hour (right).

Q-starch must be able to protect siRNA from nuclease degradation for optimal gene silencing. siRNA/Q-starch polyplex and "naked" siRNA (without carrier) were incubated with human serum (50% vol.) for several periods of time. Naked siRNA incubation with serum resulted in complete degradation after 1 hour (right panel), while, as can be seen from FIG. 5, complexation of Q-starch with siRNA at N/P=2 protects siRNA from nuclease activity even after 24 hr of incubation with the serum (left panel).

Example 6

Biological Effect of Q-Starch/siRNA Complexes on Gene Silencing

The effectiveness of the developed Q-starch-based delivery system was investigated by measuring the gene silencing efficiency in transfection experiments. The in vitro study was conducted utilizing the model cell line NCI-ADR/Res (human ovarian cancer cell line NAR), which highly expresses the P-glycoprotein (P-gp) extrusion pump, the silenced protein in the transfection experiments. The targeted gene, ABCB1, which expresses P-gp, was silenced by using a sequence-specific siRNA (siP-gp).

In the transfection experiments, the cells were treated with different formulations containing 50 nM of free siP-gp or siRNA (siP-gp or nt-siRNA) complexed with Q-starch. The transfection efficiency was measured by FACS 24 and 72 hours post-treatment. For FACS measurements, the silenced protein, P-gp, in each experimental group was fluorescently labeled by two antibodies, a primary P-gp-specific antibody and a secondary antibody labeled by FITC. In order to reduce non-specific attachments of the antibodies to cellular components, the cells were also treated by a control mixture of secondary and isotype control antibodies (data not shown). The fluorescence intensity detected from these cells was equal to the intensity of cells that were not treated with antibodies, indicating that the non-specific attachment of the antibodies was negligible. The efficiency of gene silencing is presented by percentage of gene expression and was calculated according to the following equation: % gene expression=$(RFU_{treated}-RFU_{unstained})/(RFU_{untreated}-RFU_{unstained})$, where RFU is the relative fluorescence unit and unstained relates to non-labeled cells (auto-fluorescence).

Figure 6:
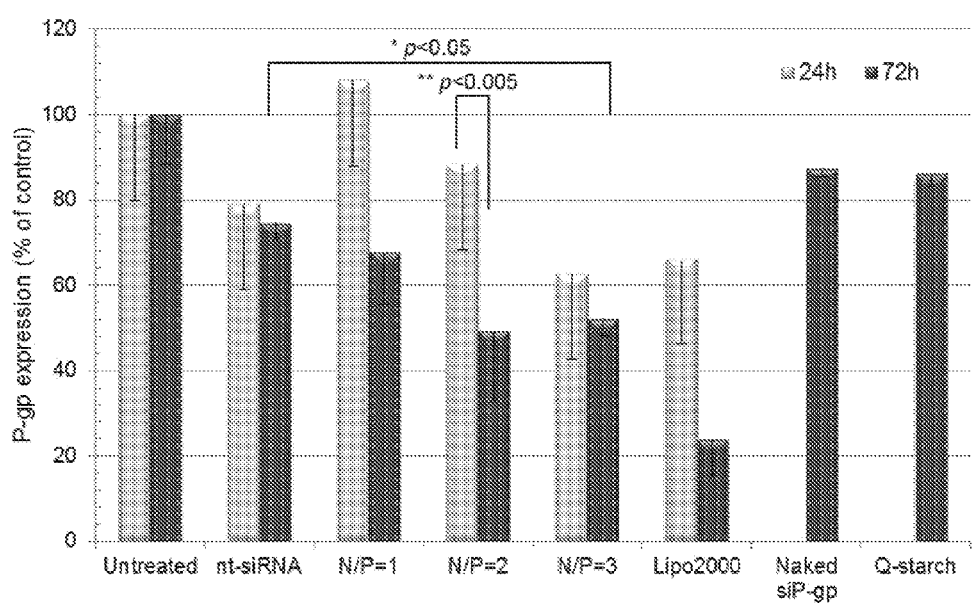
FIG. 6 shows the effect of a 24 (light bars) or 72 (dark bars) hour incubation with Q-starch-siRNA P-glycoprotein (P-gp) complexes on P-gp gene silencing in NAR cells. The Y axis shows P-gp gene expression as % of control, and the pairs of bars correspond from left to right to untreated cells (control), non-targeting (nt) siRNA complexed with Q-starch at N/P=2, complexes of Q-starch-P-gp-siRNA at N/P ratios=1, 2 and 3, cells treated with lipofectamine (Lipo2000) and P-gp-siRNA as a positive control, naked siP-gp RNA, and free Q-starch. Vertical bars represent mean±SD for three experiments. * $p<0.05$ relates to comparing N/P=3 to nt-siRNA for same time point (72 h); ** $p<0.005$ relates to comparing 24 h and 72 h of the same application (N/P=2).

As can be seen in FIG. 6, polyplexes at N/P ratio of 2 and 3 induce the most efficient P-gp gene silencing after 72 hours incubation with the NAR cells. For comparison, DNA complexes were most efficient at N/P=5 (Sieradzki et al., 2008). Compared to untreated cells, P-gp expression levels were reduced to 49% and 52% with polyplexes at N/P ratios of 2 and 3, respectively. Cells exposed to free Q-starch or naked siP-gp did not exhibit significant gene silencing, as can be seen from FIG. 6, and the reduction in P-gp expression seen in these groups (~15%) is due to non-specific silencing events that are also seen in the Q-starch/nt-siRNA experimental group. As expected, the difference in gene silencing efficiency of polyplexes at N/P ratio 2 and 3 is insignificant since both are positively charged and small enough to enable entrance into the cells and result in gene silencing. Furthermore, at N/P=1, in which full siRNA complexation with Q-starch is not established (as shown in FIGS. 2 and 3B), the silencing efficiency is reduced as expected since the transfection efficiency of naked siRNA (which is also not chemically modified) in vitro is very low because the molecule's negative charge prevents it from cellular internalization and is readily degraded by serum endonucleases (Gary et al., 2007). Complexes of Q-starch with non-targeting siRNA complexed with quaternized starch at N/P=2 indicate the off-targeting effect. Off-targeting effects in vitro were shown to be cell line and delivery platform dependent and caused up and down regulation of genes (Merkel et al. 2011). According to FIG. 6, non-targeting siRNA resulted in 26% off-target gene silencing after 72 hours. In order to evaluate Q-starch transfection efficiency, the off-target gene silencing was compared to the transfection efficiency of complexes at N/P 3. Using a paired t-test, a statistically significant difference was observed ($p<0.05$) and it seems that the complexes at N/P 3 caused a significant sequence-specific gene silencing. Complexes of siP-gp/Q-starch at N/P ratios of 2 and 3 therefore induced significant gene silencing compared to the non-targeting siRNA after 72 hours ($p<0.01$). As can be seen from FIG. 6, the silencing effect after 24 hours was much less significant, which might indicate that after 24 hr of treatment with each of the compounds, the full effect of gene silencing in NAR cells has not yet been realized.

Lipofectamine 2000, a commercially available transfection reagent, served as a positive control and resulted in 66±19% and 24±8% of gene silencing after 24 and 72 hours of incubation with NAR cells, respectively. Although highly efficient, Lipofectamine 2000 is not a therapeutic agent because of its previously reported toxicity that interferes with its therapeutic application When comparing the siRNA results to results with DNA for efficient transfection and high cell viability, a smaller amount of siRNA is required (siRNA—0.27 µg/mL, DNA—2 µg/mL) to reach higher percentage of transfection (49% transfection at N/P=2 compared with 10% for DNA, data not shown). Since a lower N/P ratio is needed for siRNA than for DNA, as explained above, the siRNA complexes are less toxic because of the lower levels of positive charges, which are potentially toxic to cells, and the presence of fewer artificial modifications.

Example 7

Cell Viability

Figure 7:
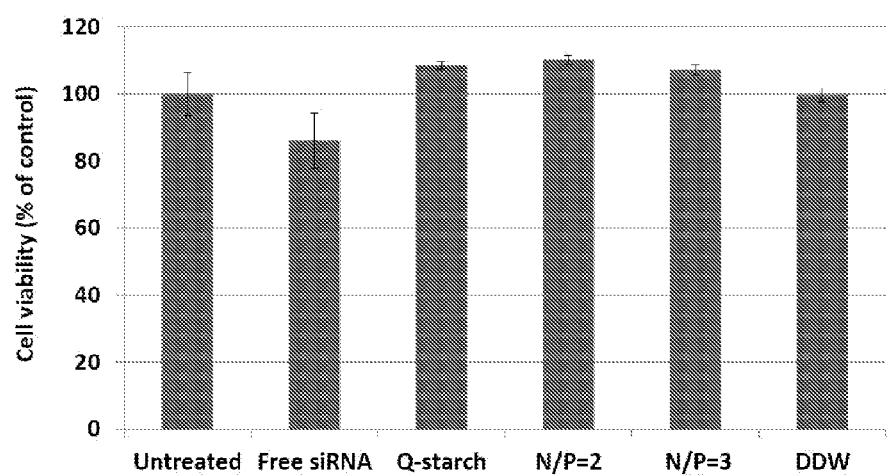
FIG. 7 shows the cytotoxic effect of a 72 hour incubation with Q-starch-siRNA complexes on NAR cells, measured as cell viability (% of control, Y axis). Left to right: no treatment (control), naked P-gp-siRNA, Q-starch complexes of P-gp-siRNA/Q-starch without siRNA and with siRNA at N/P ratios of 2 and 3, and DDW (double distilled water) negative control (the solvent of the siRNA/Q-starch complexes); siRNA concentration was 20 nM.

The toxic effect of a delivery system is one of the main parameters that should be evaluated when developing a delivery carrier. The leading motivation for using polysaccharides as delivery carriers is to address these issues. Polysaccharides are known as biocompatible materials that have low toxicity effects. For toxicity evaluation of Q-starch/siP-gp complexes, NAR cells were incubated with complexes or complex components (siRNA and Q-starch separately) for 72 hours, after which an MTT cell viability assay for cellular proliferation was conducted. The percentage of cell viability was normalized to the control group of untreated cells (100% viability); the results are summarized in FIG. 7. Cytotoxicity study of siRNA/Q-starch polyplexes at N/P ratios of 2 and 3 has found the complexes to be non-toxic compared to untreated cells. When the cells were treated with naked siRNA at the same concentration used in the polyplexes, the cell viability was lower than 90%, indicating that siRNA's toxic effect is reduced when complexed with Q-starch. For comparison, cytotoxicity with Q-starch-DNA complexes was 85% (data not shown).

Example 8

Cellular Uptake of Naked siRNA Vs. Q-Starch/siRNA Complexes

The site of action of RNAi is the cytosol, because of which, along the transfection process siRNA complexes face multiple delivery barriers including the non-permeable plasma membrane (extra-cellular barrier), endosomal escape, and decomplexation of siRNA complexes (intracellular barriers). According to FIG. 6, NAR cells exposed to complexes at N/P 1 didn't induce significant P-gp silencing through the whole transfection timeline (until 72 hours of incubation with the complexes). Also, cells exposed to complexes at N/P 2 did not induce significant P-gp silencing after 24-hour incubation with the complexes, while further incubation time with the complexes efficiently induced P-gp silencing. Our initial hypothesis was that the plasma membrane was a key barrier for siRNA delivery by Q-starch, and poor cellular uptake was presented through the whole assay for complexes at N/P=1 and through the first 24 hours for complexes at N/P=2. We therefore examined the cellular uptake of fluorescently labeled naked siP-gp$^{lab}$ and complexes of Q-starch/siP-gp$^{lab}$ at N/P=1 and 2 by a confocal microscope. During the experiment, NAR cells were treated with different formulations and monitored over a 24-hour course of treatment (siRNA concentration was the same as in transfection: 50 nM). Representative confocal images are shown in FIG. 8.

Figure 8A:
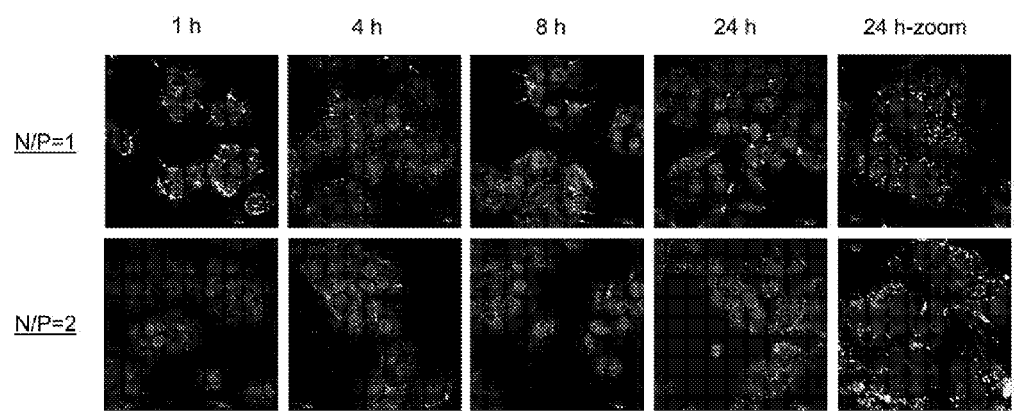

DAPI (blue) staining defines the nucleus area and cell borders are labeled by WGA Alxa 555® (yellow) staining in order to demonstrate intracellular trafficking of the complexes. FIG. 8 shows uptake of complexes after 1, 4, 8, and 24 hours of incubation, and indicates that complexes at N/P=1 have relatively low uptake capabilities and only a few complexes (siRNA labeled in red and pointed to by a white arrow in FIG. 10A top panel, N/P=1, 1-24 h) were visualized inside the cell cytoplasm after 24 hours of study (FIG. 8A). As mentioned above, the uptake of complexes at N/P=1 is insufficient and the plasma membrane constitutes a key barrier for negatively charged particles that don't bear targeting ligands. The association of these particles with the anionic membrane is a limiting step in the transfection and our hypothesis was confirmed. On the other hand, complexes at N/P=2 showed substantial uptake by NAR cells. After 1 hour of complex incubation (FIG. 8A lower panel, N/P=2) we observed that not all the cells showed uptake and the scanned fields were non-homogenous regarding complex uptake. Comparing it to images of treatment by N/P=1 along all 24 h treatments, complexes at N/P=2 showed a significant entrance after only 1 hour of incubation. However, after 4 hours incubation with the complexes, most of the cells presented uptake, and after 24 hours, significant complex penetration was shown. In order to emphasize the necessity of Q-starch as an siRNA delivery vector, FIG. 8B shows a side-by-side comparison of cells treated by naked siP-gp$^{lab}$ and by Q-starch/siP-gp$^{lab}$ at N/P=2 after 24 hours of incubation. The massive uptake of complexes is shown and that the complexes are mainly detected inside the cytoplasm. Additionally, it seems that naked siP-gp$^{lab}$ entrance was negligible, and entrapment by Q-starch significantly improved its potential to enter NAR cells and finally integrate into the RNAi mechanism. These results suggest, in contrast to our hypothesis, that the membrane barrier didn't inhibit the gene silencing process that was observed during the first 24 h of treatment by complexes at N/P=2 (FIG. 6). This could imply that the rate limiting step for the transfection was intracellular. Either the complexes that entered the cells escaped the endosome compartment 24-72 hours post-exposure, or dissociation of siRNA from its carrier limited the transfection kinetics.

Example 9

Figure 9:
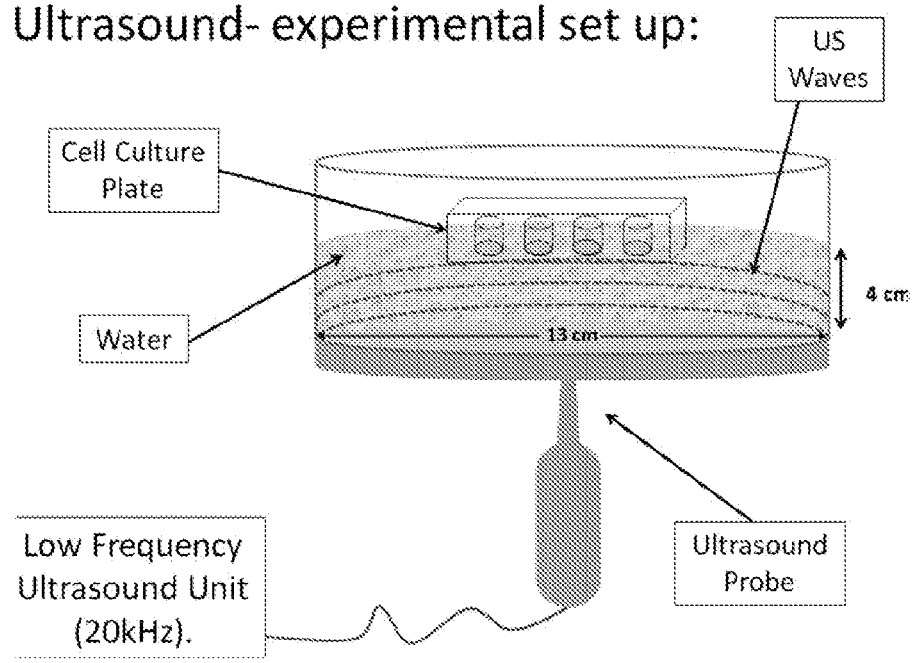
FIG. 9 shows the ultrasound experimental setup for cell culture experiments. Cells together with complexes are placed on top of a foamed polyethylene layer in an ultrasonic 13 cm plate horn (20 kHz Misonix-ultrasonic liquid processor S4000-010, max intensity 600 W) filled with 4 cm water and ultrasound is applied.
Figure 10:
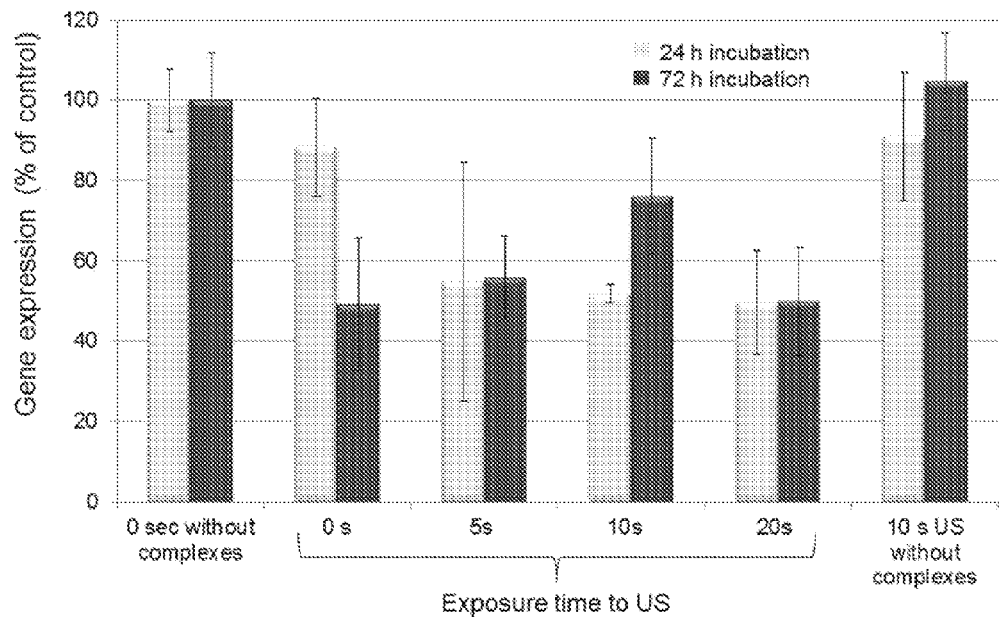
FIG. 10 shows the effect of ultrasound (US) on transfection efficiency with Q-starch/siRNA polyplexes at N/P=2. Ultrasound was applied to NAR cells after 30 min of incubation with the polyplexes. Gene knockdown was compared to untreated cells (first pair of bars from left, 0 sec without complexes). Incubation time was carried out for 24 hours (light bars) or 72 hours (dark bars). The second through fifth pairs of bars from left correspond to 0, 5, 10 and 20 seconds of exposure to ultrasound. The pair of bars on the right corresponds to treatment with ultrasound for 10 seconds without complexes. The Y axis is % gene expression compared to the untreated cells control.

Biological Effect of Ultrasound (US) on Gene Silencing with Complexes of Q-Starch/siRNA In Vitro The ultrasound experimental setup is outlined in FIG. 9 and described in the methods section. The effect of gene knockdown with polyplexes at N/P=2 was found to be reduced with the reduction of polyplex incubation time. For example, for N/P=2, 24 hours incubation with no ultrasound results in approximately 90% expression (FIG. 6, left bar in the 4$^{th}$ pair from left and FIG. 10, left bar of 2$^{nd}$ pair from left), while 72 hours incubation time results in approximately 50% expression (FIG. 6, right bar in the 4$^{th}$ pair from left). This might indicate that after 24 hr of treatment with each of the compounds, the full effect of gene silencing in NAR cells has not yet been realized. As can be seen in FIG. 10, treatment of cells with polyplexes and ultrasound 30 minutes after addition of the complexes resulted in ~50% gene silencing even after 24 hours of incubation time. The addition of ultrasound exposure to the transfection treatment counteracted the effect of incubation time on gene silencing, so the treatment with polyplexes and ultrasound results in a speedier response to the treatment, expressed by gene silencing, compared to treatment without ultrasound. FIG. 10 also shows that longer times of exposure to ultrasound (72 hours) did not enhance gene silencing efficiency.

Example 10

The Effect of Ultrasound Exposure on the Viability of NAR Cells

Figure 11:
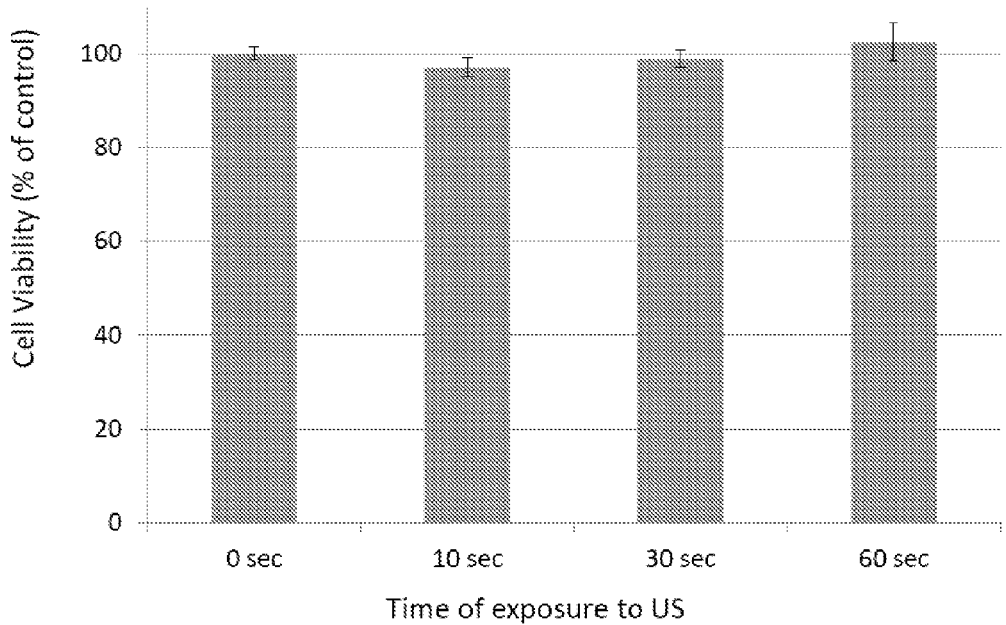
FIG. 11 shows cell viability results for NAR cells treated with ultrasound. The bars (left to right) correspond to 0, 10, 30 and 60 seconds exposure to ultrasound (n=6). The Y axis is % cell viability compared to the control (0 seconds exposure).

As shown in FIG. 11, ultrasound exposure didn't affect cell viability even after 60 seconds of exposure to ultrasound, therefore gene silencing experiments utilizing ultrasound are not expected to have increased cell death.

Example 11

The Effect of Ultrasound Exposure on Uptake of Complexes into NAR Cells

In order to determine whether the membrane permeability barrier was affected by the ultrasound (US), the effect of ultrasound on cellular uptake of Q-starch/siRNA complexes was examined. NAR cells were exposed to complexes of siRNA (labeled in red by cy5) and Q-starch, and ultrasound was applied 30 min after adding the complexes for 10 sec in the same conditions as for the gene silencing experiments (2.14 mW/cm$^2$). 60 min after ultrasound was triggered the cells were visualized with a confocal microscope.

Figure 12A:
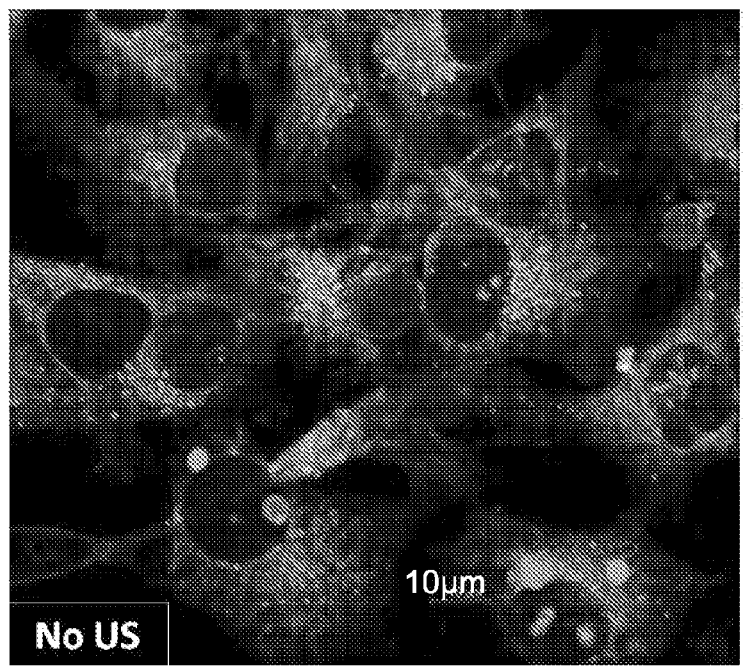
FIGS. 12A-12B show that ultrasound enhances uptake of Q-starch/siRNA complexes into cells. NAR cells were incubated with complexes at N/P=2, and either ultrasound (2.1 mW/cm$^2$) was applied after 30 min (B), or no ultrasound was applied (A). Cellular uptake was visualized 1.5 hours after incubation of the complexes with the cells. Cell membrane was labeled with FM® Lypiphilic Styryl dye (green) and siRNA was labeled with Cy5 (red).
Figure 12B:
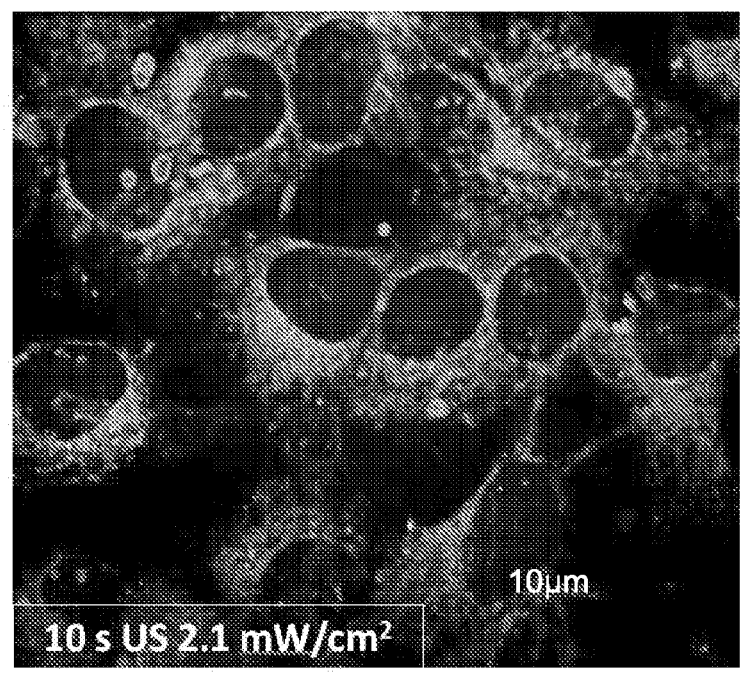

Cells were labeled by the membrane dye FM® Lypiphilic Styryl dye, defining the membrane and the cytoplasm area in green and the nucleus area was not labeled (FIG. 12). The results demonstrate that 1.5 hours post-transfection, labeled complexes were detected within the cellular cytoplasm as round particles with clear borders. Since naked siRNA cannot enter the cells by passive transport through the membrane (as discussed in Example 8 above), it is reasonable to assume that the siRNA that is detected within the cells is either complexed with Q-starch or may be in the free form if decomplexation from the carrier has already occurred inside the cells.

Although, as shown in FIG. 12, ultrasound increased the intensity of the red signal within the nuclei of NAR cells, demonstrating increased transport of siRNA or siRNA complexes, based on the confocal microscopy images it seems that Q-starch/siRNA complexes enter the cells effectively in the first hours of transfection even without the aid of the ultrasound. In view of this, the membrane is probably not a significant barrier for transfection. Ultrasound may have influenced the membrane's permeability; however, enhanced transport was not necessarily enhanced since the complexes already have the ability to efficiently enter the cells without the influence of ultrasound.

The enhanced kinetics of gene silencing after ultrasound exposure (as seen in FIG. 10) could be the result of intracellular effects of ultrasound. As mentioned, ultrasound may affect the endosomal escape stage and the decomplexation stage of transfection. It was previously shown (Sieradzki et al., 2008) that the rate limiting step in gene delivery with the same carrier was also the endosome escape of the complexes. It was mainly confirmed by the increased transfection efficiency demonstrated after Q-starch was modified by a lysosomotropic agent. Since the endosome is surrounded by a membrane, the disruption of the endosome can be influenced by ultrasound and as a result the complexes are released to the cell cytoplasm.

Another possible scenario is that the decomplexation stage was affected by ultrasound. Previous reports, including one from the present inventors, showed that ultrasound has been used to trigger the release of drugs from polymeric carriers. If the electrostatic interactions between Q-starch and siRNA are strong enough so that the decomplexation stage is the rate-limiting step of the transfection, ultrasound might assist in separating Q-starch from siRNA and releasing siRNA to the RNAi pathway.

It is also possible that ultrasound affected complex entrance into the nucleus of NAR cells. If so, ultrasound must have affected more than one barrier, which is certainly possible and probably the case here. The RNAi pathway is carried out in the cellular cytoplasm and the nucleus does not participate in this machinery. Therefore increased transport to the nucleus should not increase the transfection kinetics in gene silencing. However, according to FIG. 10, the silencing efficiency was clearly affected so ultrasound must have influenced multiple barriers along the transfection Example 12

Cellular Uptake of Q-Starch/siRNA Complexes in Keratinocytes

HaCaT Keratinocyte were seeded in a 12-well plate with a glass coverslip at a density of 6*10$^4$ cells/well in culture medium (FBS, L-glutamine and Penicillin-streptomycin in Minimum Essential Medium (MEM-EAGLE)) 24 hours before transfection, and reached 40-50% confluence on the day of transfection. On the day of transfection, the culture medium was removed and 900 µL of serum and antibiotic free medium (L-glutamine in MEM-EAGLE) were added to each well. The cells were incubated for 4.5 hours with various concentrations (5 nM to 1 µM) of Q-starch/siRNA complexes labeled with Cy5 at N/P=2 (FIG. 13). 1 µM of naked siRNA was used as negative control (panel d), and a commercial carrier, X-tremeGENE® (Roche Applied Science) was used at a complex concentration of 5 nM as positive control (panel e).

Figure 13:
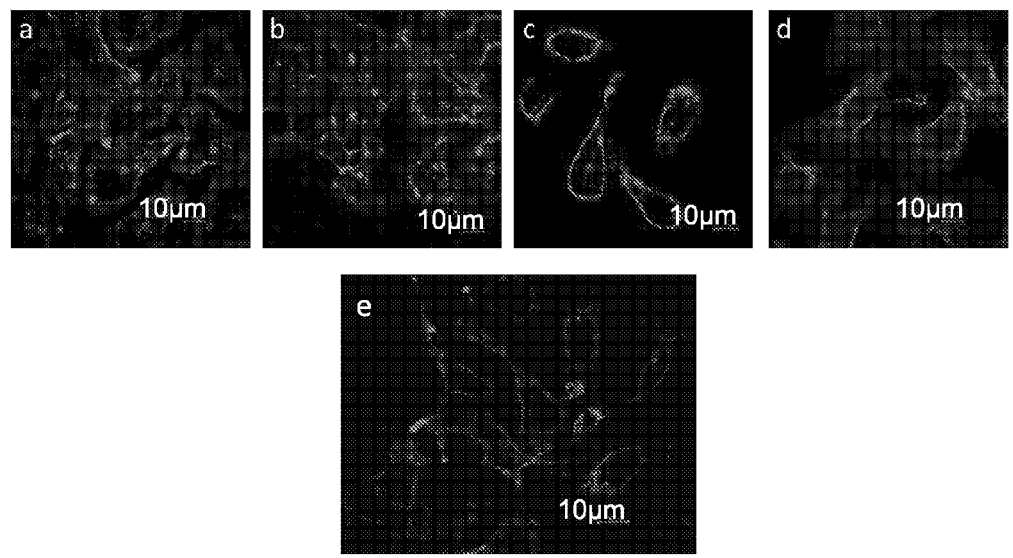
FIG. 13 shows cellular uptake of complexes by keratinocytes. Keratinocyte HaCaT cells were incubated for 4.5 hr with Q-starch/siRNA complexes at N/P=2 (panels a-c) or with 1 µM naked siRNA (panel d). A commercial carrier, X-tremeGENE® (Roche Applied Science) was used at 5 nM as positive control (panel e). Cellular uptake of complexes was visualized by confocal microscopy. Concentration of the complexes were 1 µM (A), 0.5 µM (B), and 0.05 µM (C). The cell membrane was labeled with WGA Alexa Fluor® 555 in red and the siRNA was labeled with Cy5 (blue).

The results presented in FIG. 13, panel a show that the Q-starch/siRNA complexes were capable of entering the human keratinocyte HaCaT cells, while naked labeled siRNA did not enter these cells, as shown in panel d. Entry into the cells was dependent on concentration, as a large number of complexes could be visualized inside the cells at complexes concentration of 1 µM (panel a), while some could be visualized at 0.5 µM (panel b), and practically none could be visualized at 0.05 µM (panel c). The positive control shows entry of complexes into the cells at a concentration of 5 nM (panel e).

Example 13

Ultrasound Induces Enhanced Cellular Uptake of Q-Starch/siRNA Complexes in Keratinocytes HaCaT Keratinocyte were treated as in the previous example, and the 12-well tissue culture plate was placed in an aqueous medium above an ultrasound plate horn bath (as shown in FIG. 9). Ultrasound application of 20 seconds at 2.14 mW/cm$^2$ was carried out 60 minutes after adding the Q-starch/siRNA complex solution, in order to assess the dynamic of the complexes entry. After incubation of 4 hours with the complexes, the cells were fixed with 4% paraformaldehyde and the membrane was labeled with a fluorescent dye, Wheat Germ Agglutinin, Alexa Fluor® 555 Conjugate. The uptake of complexes was determined by confocal microscopy.

Ultrasound affects cell membrane permeability causing increased cellular internalization, and hence, increase the efficiency of the delivery mechanism.

The results (FIG. 14) show that at a concentration of 0.05 µM, complexes can be visualized in the cells after ultrasound treatment (14A), but no complexes could be visualized in cells transfected with 0.05 µM of complexes and not treated with ultrasound (14B, as done in Example 12). These results confirmed the beneficial effect of ultrasound application as an added means to reach higher efficiency of entrance of complexes to HaCaT cell line. As explained, ultrasound application allows introducing into the cells siRNA concentration at two orders of magnitude lower than established for transfection without ultrasound.

Example 14

Effect of Ultrasound on the Entry of Q-Starch/siRNA Through Porcine Skin

Efficient topical treatment for skin disorders such as psoriasis will have to allow siRNA to be efficiently delivered across the stratum corneum, and enable functional uptake by keratinocytes.

Figure 15:
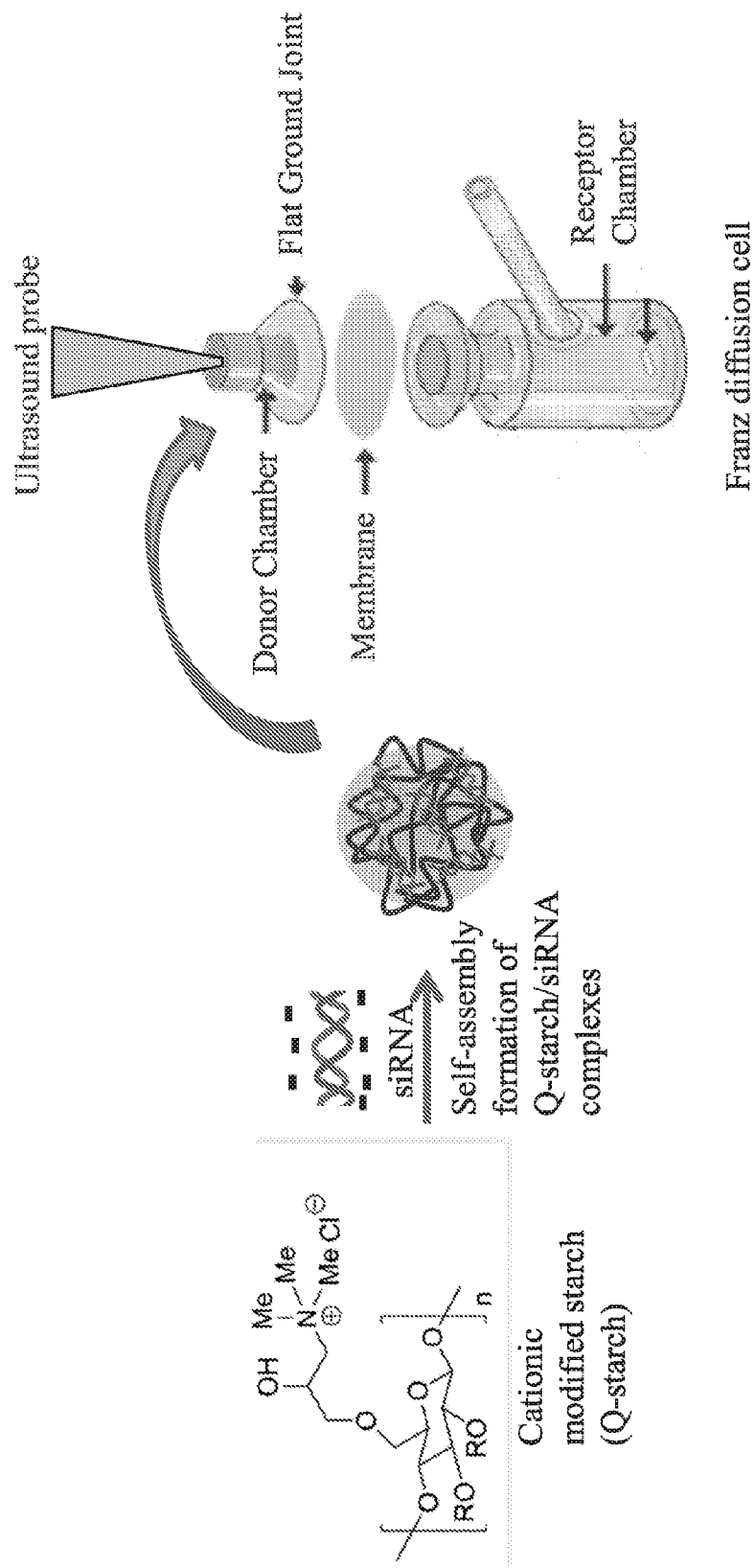
FIG. 15 shows a scheme for the uptake of Q-starch/siRNA complexes by skin tissue in a diffusion cell with ultrasound to increase skin permeability. Cationic modified starch (Q-starch) is incubated with siRNA and Q-starch/siRNA complexes are self-assembled. The skin is mounted with the stratum corneum facing the donor compartment. The donor compartment is filled with coupling medium (1% sodium lauryl sulfate (SLS) in PBS) while the receiver compartment is filled with PBS. One conductivity electrode is placed in the lower chamber and the other electrode is placed in the ultrasound medium. Ultrasound is applied until conductivity reached 40-60 fold of the initial conductivity and the coupling medium is replaced with Q-starch/siRNA complexes solution dissolved in water and protected from light (in order to eliminate a possibility of photo bleaching).

The experiments were performed in diffusion cells composed of 8.5 mL donor and 5.5 mL receiver compartments with a transport cross-section area of 2.27 cm$^2$ (FIG. 15). The integrity of each skin sample was measured by means of conductivity. The skin was mounted with the stratum corneum facing the donor compartment. The donor compartment was filled with coupling medium 1% sodium lauryl sulfate (SLS) in PBS while the receiver compartment was filled with PBS. One conductivity electrode was placed in the lower chamber and the other electrode was placed in the ultrasound medium. Ultrasound application was for 10 minutes at 8.2 W/cm$^2$ and was stopped when conductivity reached 40-60 fold of the initial conductivity. Ultrasound operated at a frequency of 20 KHz equipped with a 13 mm probe, located in the donor compartment. Temperature measurements were taken during all ultrasound experiments. Ultrasound coupling medium was replaced every 30 sec, in order to eliminate temperature influence. After ultrasound application, the coupling medium was replaced with Q-starch/siRNA complexes solution dissolved in water and protected from light (in order to eliminate a possibility of photo bleaching). The cells were incubated with complexes for 15 hours. In all experiments, a control group was treated by a similar experimental procedure with ultrasound power outputs set to zero. After the experiment, skin samples were sent to histopathology for staining and testing by confocal microscopy.

Figure 14A:
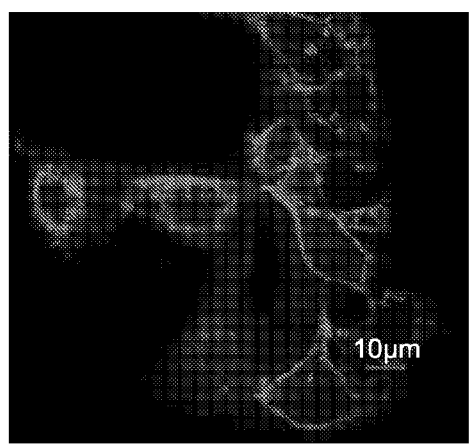
FIGS. 14A-14B show increased cellular uptake of complexes by keratinocytes after treating with ultrasound. HaCaT Keratinocytes were incubated for 4 hours with Q-starch/siRNA complexes at N/P=2. A. Ultrasound was applied for 20 sec at 2.14 mW/cm$^2$ 60 min after complexes incubation; B. No ultrasound application. Total siRNA concentration in the medium was 0.05 µM. The cell membrane was labeled with WGA Alexa Fluor® 555 in red and the siRNA was labeled with Cy5 (blue).
Figure 14B:
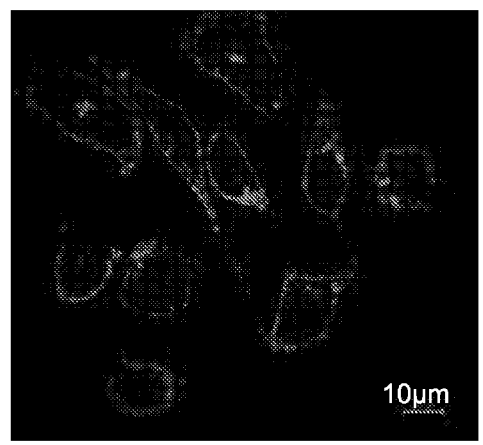
Figure 16A:
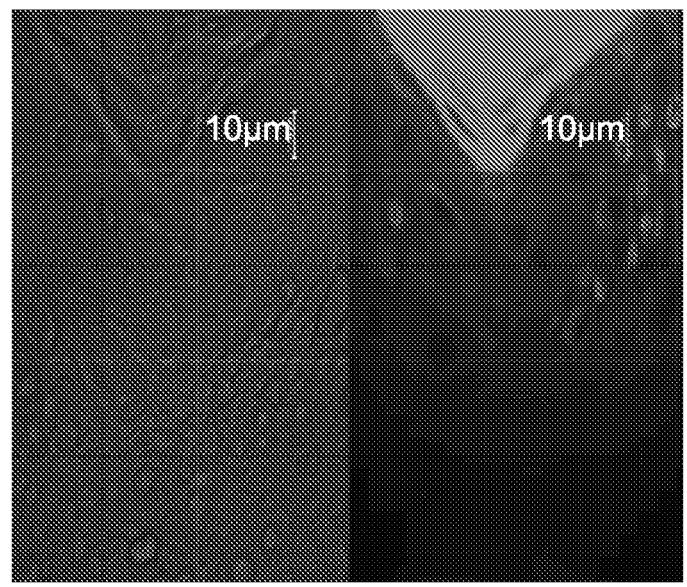
FIGS. 16A-16B show that ultrasound application on porcine skin induces enhanced uptake of complexes into skin tissue. Confocal images of porcine skin cross section after 15 hr of incubation with Q-starch/siRNA complexes are shown. A. The skin was pre-treated with ultrasound application of 10 minutes at 8.2 W/cm$^2$; B. Without ultrasound pre-treatment. siRNA was labeled with Cy5 (red).
Figure 16B:
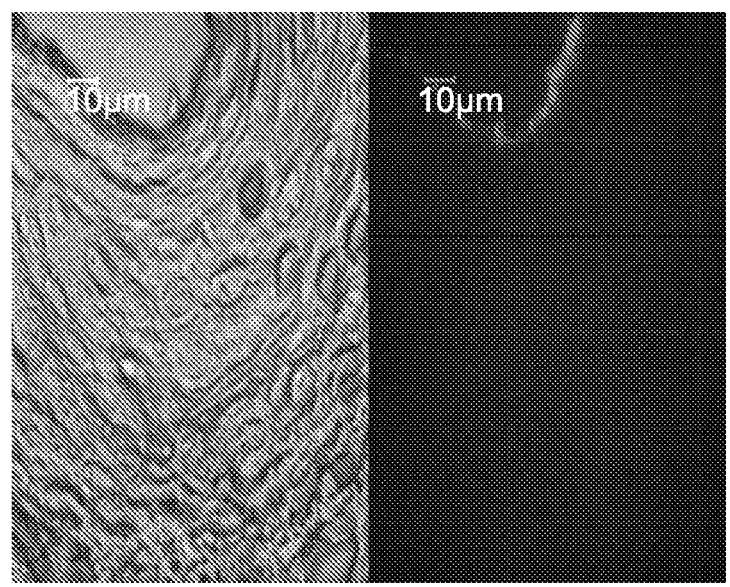

The results verified the ability of ultrasound to enhance transdermal delivery (FIG. 16), as well as cell entrance (as demonstrated in FIG. 14). The results show that complexes could be visualized at the basal keratinocyte cell layer of the epidermis when transfected after ultrasound treatment, but not when ultrasound output was set to zero. This confirms that ultrasound application on porcine skin enables transdermal delivery as well as entrance of complexes through the stratum corneum.

This efficient transdermal delivery across the stratum corneum and possibly enhanced ability of uptake by keratinocytes, enables siRNA uptake by keratinocytes and therefore should allow efficient topical treatment for skin disorders such as psoriasis by the method of the invention.

Example 15

Q-Starch/miRNA Complex Formation microRNAs (miRNAs) are small non-coding RNA molecule (about 22 nucleotides) found in plants, animals, and some viruses, which functions in transcriptional and post-transcriptional regulation of gene expression. Aberrant expression of miRNAs has been implicated in numerous disease states, and miRNA-based therapies are under investigation. Therefore the inventors examined whether the methods of the invention could also be applied to miRNA transfection.

Figure 17:
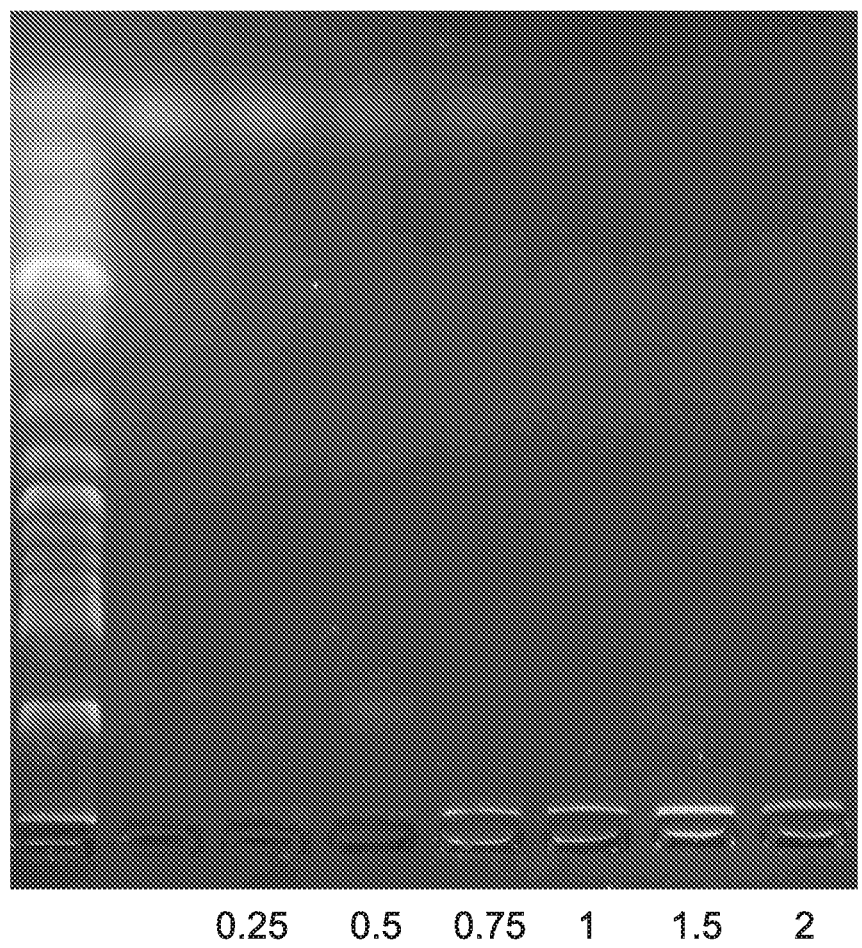
FIG. 17 shows Q-starch (quaternized starch)-miRNA (micro-RNA) complex formation by gel electrophoresis. Lanes: (left to right): DNA ladder, free miRNA, Q-starch-miRNA complexes at the indicated N/P ratios: 0.25, 0.5, 0.75, 1, 1.5, and 2. Free miRNA size is 22 bp and the complexed miRNA is seen around the wells.

Similarly to siRNA, Q-starch/miRNA complex formation is based on electrostatic interaction between positively charged Q-starch and negatively charged miRNA. The desired N/P ratio is the ratio in which Q-starch is able to form a condensed polyplex with miRNA and none of the miRNA remains free. Free miRNA at gel electrophoresis runs along the gel towards the positive electrode and can be visualized by the bright band that matches its size of 22 base pairs as determined by the DNA ladder (FIG. 17, left lane). As N/P ratio increases, free fragments of miRNA are entrapped within the Q-starch/miRNA complexes and the free miRNA band gets less bright. The complexes are bigger in size than free miRNA and cannot run along the gel because of its agarose density. The minimal N/P ratio for full complexation was 1, since no free miRNA could be seen in the lane (FIG. 17, third lane from right).

Example 16

Q-Starch/miRNA Complex Characterization

Figure 18A:
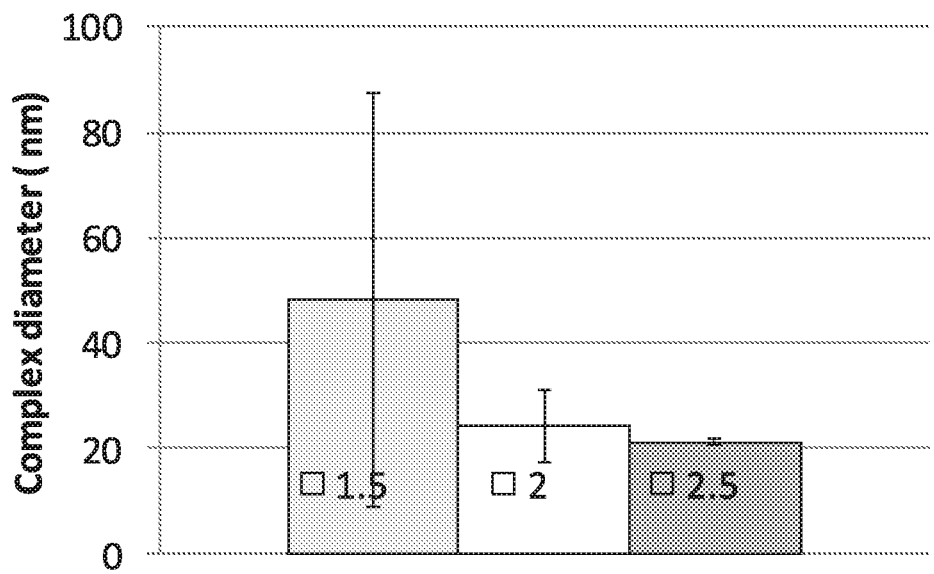
FIGS. 18A-18B show Q-starch-miRNA self-assembled nanoparticles at various N/P ratios. The bars correspond (from left to right) to N/P ratios of 1.5 (light gray), 2 (white) and 2.5 (dark gray). A. Mean particle diameter. B. Mean zeta potential. The numbers represent an average of three preparations (n=3). The lines on each bar represent standard deviation.
Figure 18B:
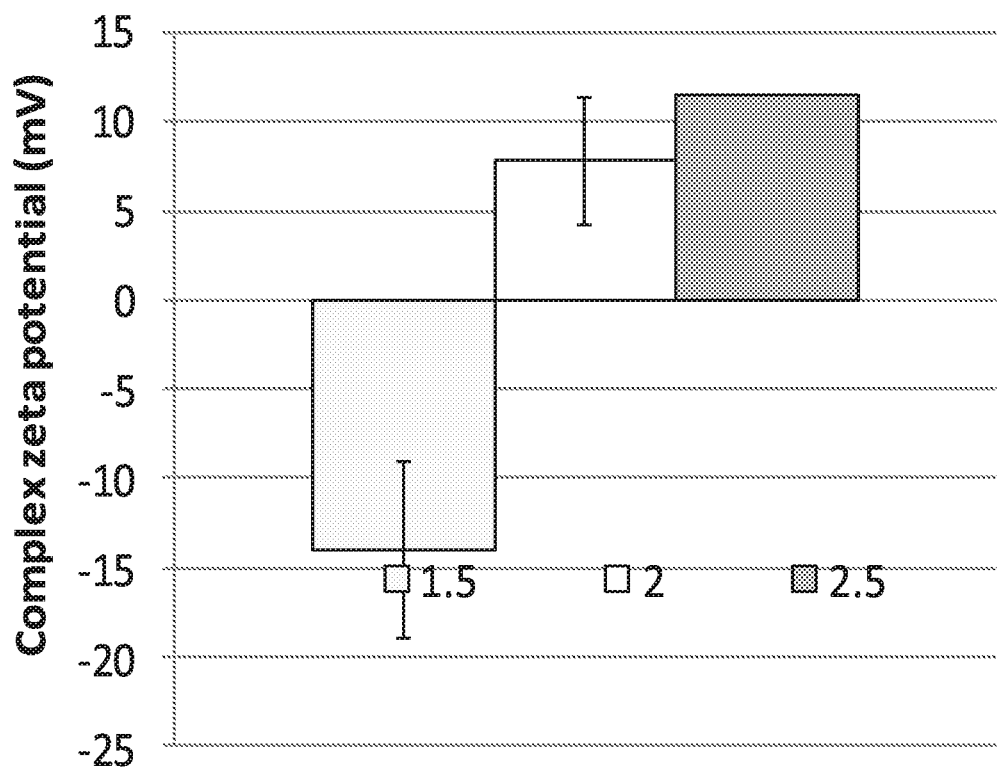
Figure 19A:
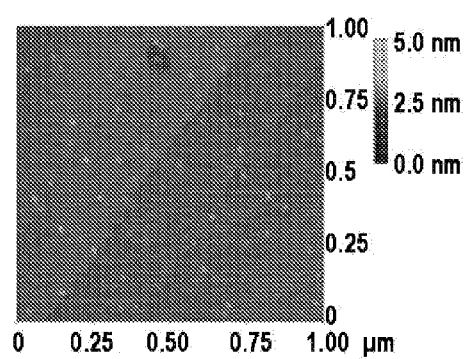
FIGS. 19A-19D show an atomic force microscope scan of Q-starch-miRNA complexes at N/P ratio of 1.5 (A), 2 (B) and 2.5 (C), and Q-starch without miRNA (D).
Figure 19B:
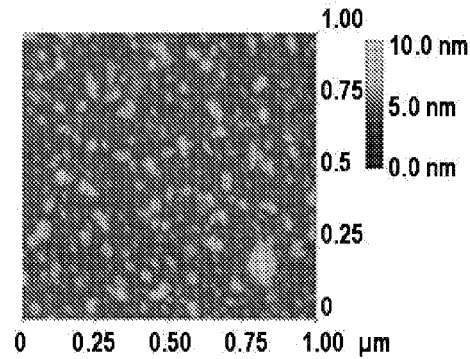
Figure 19C:
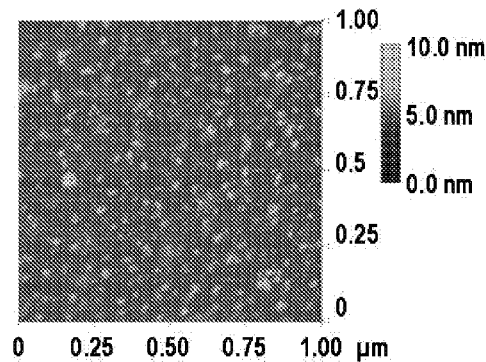
Figure 19D:
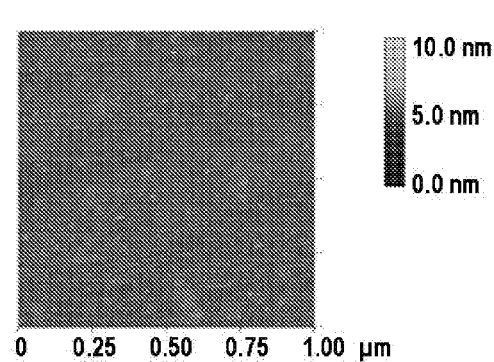

The diameter and charge of the miRNA/Q-starch polyplexes are shown in FIG. 18 for N/P ratios of 1.5, 2 and 2.5. As seen in FIG. 18A, the mean size of self-assembled Q-starch/miRNA complexes, as measured by Dynamic Light Scattering (DLS), was small (between 15.0-35.0 nm in diameter at N/P=2). At an N/P ratio of 1.5 the zeta potential is negative (FIG. 18B) since free fragments of miRNA are still present in the polyplex solution, while above that ratio, the zeta potential turns positive. AFM scan confirmed the DLS results, as shown in FIG. 19. According to particle analysis by AFM, the mean size of complexes at a ratio of N/P=2 was in the range of 22.5-46.7 nm and the mean diameter was 34.83 nm. The relatively small complex size (diameter smaller than 100 nm, FIG. 19B) and positive charge of the miRNA polyplexes at N/P ratio of 2 and above indicate the capability of these complexes to enter cells through endocytosis.

Example 17

Effect of Ultrasound on the Entry of Q-Starch/miRNA Complexes Through Porcine Skin The experiments were performed in diffusion cells composed of 8.5 mL donor and 5.5 mL receiver compartments with a transport cross-section area of 2.27 cm$^2$ (FIG. 15). The integrity of each skin sample was measured by means of conductivity. The skin was mounted with the stratum corneum facing the donor compartment. The donor compartment was filled with coupling medium 1% sodium lauryl sulfate (SLS) in PBS while the receiver compartment was filled with PBS. One conductivity electrode was placed in the lower chamber and the other electrode was placed in the ultrasound medium. Ultrasound application was for 7 minutes at 8.2 W/cm$^2$ and was stopped when conductivity reached 40-60 fold of the initial conductivity. Ultrasound operated at a frequency of 20 KHz equipped with a 13 mm probe, located in the donor compartment. Temperature measurements were taken during all ultrasound experiments. Ultrasound coupling medium was replaced every 30 sec, in order to eliminate temperature influence. After ultrasound application, the coupling medium was replaced with Q-starch/miRNA complexes solution dissolved in water and protected from light (in order to eliminate a possibility of photo bleaching). The cells were incubated with complexes for 19 hours. In all experiments, a control group was treated by a similar experimental procedure with ultrasound power outputs set to zero. After the experiment, skin samples were sent to histopathology for staining and testing by confocal microscopy.

Figure 20A:
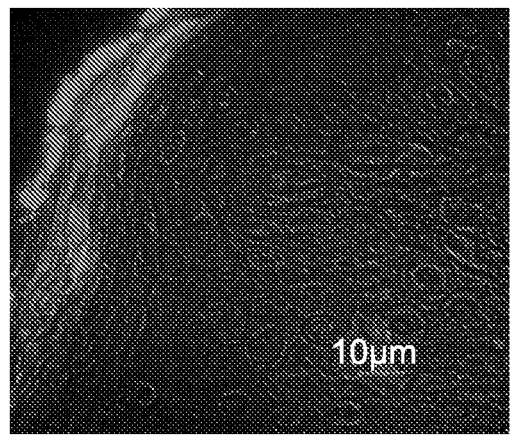
FIGS. 20A-20B show that ultrasound application on porcine skin induces enhanced uptake of complexes into skin tissue. Confocal images of porcine skin cross section after 19 hr of incubation with Q-starch/miRNA complexes at N/P ratio=2 are shown. A. The skin was pre-treated by ultrasound application of 7 minutes at 8.2 W/cm$^2$ prior to adding the complexes; B. Without ultrasound pre-treatment. miRNA was labeled with Cy3 (red).
Figure 20B:
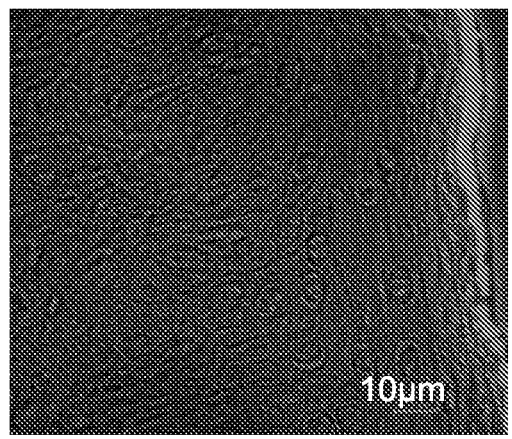

The results, shown in FIG. 20, verified the ability of ultrasound to enhance transdermal delivery. The results show that complexes could be visualized at the basal keratinocyte cell layer of the epidermis when transfected after ultrasound treatment, but not when ultrasound output was set to zero. This confirms that ultrasound application on porcine skin enables transdermal delivery as well as entrance of complexes through the stratum corneum. This efficient transdermal delivery across the stratum corneum and possibly enhanced ability of uptake by keratinocytes, enables miRNA uptake by keratinocytes and therefore should allow efficient topical treatment for skin disorders such as psoriasis by the method of the invention.

Example 18

In Vivo Experiments with a Psoriasis Mouse Model

Psoriasis mouse models are generated as described in J. Gudjons son et al., 2007, Mouse models for psoriasis, J. Invest. Dermatol. 127(6):1292-1308. After shaving the mouse back, ultrasound is applied to the mouse skin on top the psoriatic plaque. The ultrasound medium (1% SLS in PBS) is placed in a small chamber on top of the psoriatic area. Temperature measurements are taken during all ultrasound experiments. Ultrasound medium is replaced every 10-40 sec, in order to eliminate temperature influence. To evaluate the permeability of the skin, conductivity measurements are conducted during ultrasound exposure. One conductivity electrode is placed subcutaneously and the other electrode is placed in the ultrasound medium. The ultrasound application is stopped when conductivity reaches 40-60 fold of the initial conductivity. At the end of the sonication an effective amount of a solution of Q-starch/miRNA complexes at N/P=2 is placed inside a small chamber that is located on the skin.

It is expected that treatment with the Q-starch-miRNA complexes in which the miRNA is directed to a protein known to be involved in psoriasis will reduce or completely stop the rapid differentiation of basal skin cells, and that the red skin will become healthier and assume a lighter, pink color, and that the scales will disappear.

Example 19

In Vivo Experiments on a Mouse Model of Laryngeal Cancer

In vivo experiments are conducted on a mouse model bearing a human laryngeal tumor. To generate the mouse model, Hep2 human laryngeal tumor cells (2×10$^6$/150 µl) are inoculated subcutaneously into the flanks of a nude mouse, and establishment of palpable tumors is confirmed. A solution of complexes of Q-starch and siRNA directed to the STAT3 gene at N/P=2 are injected percutaneously into the tumor. Ultrasound is applied before and/or one hour after injection of the complexes. Some of the mice may be exposed to additional ultrasound treatments 1-4 days after complex injection. For ultrasound application, animals are anesthetized and ultrasound is applied at the site of the tumor. The ultrasonic probe is placed on top of the tumor using ultrasound coupling medium or gel. Ultrasound is applied at an intensity of 5.9 W/cm$^2$ for 120 seconds at a continuous mode. The intensity and duration of exposure to ultrasound may be altered in order to achieve an effective treatment.

It is expected that the tumor size will be reduced as a result of the treatment.

Example 20

Treating a Patient Having a Cancerous Tumor with siRNA/Quaternized Starch Complex A patient suffering from a tumor is treated by administering by an intratumoral injection a therapeutically effective amount of KSP (kinesin spindle protein)-siRNA complexed with quaternized starch at N/P ratio 2. It would be expected that the patient would improve his/her condition or recover.

Example 21

Treating a Patient Having a Tumor with siRNA/Quaternized Starch Complexes and Ultrasound A patient suffering from a tumor is treated by administering by intravenous (i.v.) injection a therapeutically effective amount of KSP-siRNA complexed with quaternized starch at N/P ratio 2. After accumulation of the complexes at the tumor (around 24 h from i.v. injection), a high intensity focused ultrasound (HIFU) is applied at a therapeutically effective intensity for a therapeutically effective time period at the tumor site. It would be expected that the patient would improve his condition or recover.

Example 22

Treating Psoriasis in a Human Patient with siRNA/Quaternized Starch Complexes and Ultrasound A patient having psoriasis is treated by topically administering a therapeutically effective amount of Bcl-xL-siRNA complexed with quaternized starch at a ratio of N/P=2 on top of the psoriatic lesion. First, ultrasound is applied topically at the psoriatic lesion at a therapeutically effective intensity. To evaluate the permeability of the skin, conductivity measurements are conducted during ultrasound exposure. One conductivity electrode is the ultrasound probe and the other electrode is placed on the body of the patient. The ultrasound application is stopped when conductivity reaches 40-60 fold of the initial conductivity. A solution (which can be in the form of an ointment) containing the complexes is applied to the skin during or after the use of ultrasound.

It would be expected that the patient would improve his condition or recover.

Example 23

Treating Asthma in a Human Patient with siRNA/Quaternized Starch Complexes

An asthma patient is treated by inhalation of a therapeutically effective amount of Syk kinase-siRNA complexed with quaternized starch. It would be expected that the patient would improve his condition compared to treatment with naked siRNA which is currently undergoing clinical trials.

REFERENCES

Azzam T., Eliyahu H., Makovitzki A., Linial M., Domb A. J., Hydrophobized dextran-spermine conjugate as potential vector for in vitro gene transfection. J. Control Release, 2004, 96(2): 309-23.

Gary D. J., Puri N., Won Y., Polymer-based siRNA delivery: Perspectives on the fundamental and phenomenological distinctions from polymer-based DNA delivery, Journal of Controlled Release, 2007, 121:64-73.

Geresh S., Dawadi, R. P., Arad S. (M.), Chemical modifications of biopolymers: quaternization of the extracellular polysaccharide of the red micralga Porphyridium sp. Carbohydrate polymers, 2000. 43: 75-80.

Lee M., Nah J. W., Kwon Y., Koh J. J., Ko K. S., Kim S. W., Water-soluble and low molecular weight chitosan-based plasmid DNA delivery. Pharm. Res. 2001, 18(4): 427-31.

Lerman G. et al., 2011, Small-interfering RNA targeted at antiapoptotic mRNA increases keratinocyte sensitivity to apoptosis, Brittish Journal of Dermatology, 2011, 164(5): 947-956.

Mansouri S., Lavigne P., Corsi K., Benderdour M., Beaumont E., Fernandes J. C., Chitosan-DNA nanoparticles as non-viral vectors in gene therapy: strategies to improve transfection efficacy. Eur. J. Pharm. Biopharm. 2004, 57(1): 1-8.

Merkel O. M., Beyerle A., Beckmann B. M., Zheng M., Hartmann R. K., Stoeger T., Kissel T. H., Polymer-related off-target effects in non-viral siRNA delivery, Biomaterials, 2011, 32:2388-2398.

Schaffer D. and Lauffenburger D. A., Targeted Synthetic Gene Delivery vectors, Curr. Opin. Mol., Therapeutics, 2000, 2(2): 155-161.

Sieradzki R., Traitel T., Goldbart R., Geresh S., Kost J., 2008, Development and characterization of quaternized starch as a carrier for gene therapy applications, PhD thesis.

Xu N. et al., MiR-125b, a MicroRNA Downregulated in Psoriasis, Modulates Keratinocyte Proliferation by Targeting FGFR2. Journal of Investigative Dermatology, 2011, 131:1521-1529.

What is claimed is:

1. A complex for the delivery of a siRNA or miRNA, comprising the siRNA or miRNA complexed with a quaternized polysaccharide, said polysaccharide being selected from the group consisting of starch, amylose, amylopectin, galactan and dextrin.

2. The complex of claim 1, wherein the molar ratio of positively charged amine groups on said quaternized polysaccharide and negatively charged phosphates on said siRNA or miRNA backbone is in a range of about 0.1-100 or about 1-5, or said ratio is about 2.

3. The complex of claim 1, wherein said quaternized polysaccharide is quaternized starch.

4. The complex of claim 3, wherein the molecular weight of said starch is in a range selected from the group consisting of about $10^3$ to about $10^8$ daltons, about $10^4$ to about $10^5$ daltons and about $10^4$ to $5 \times 10^4$ daltons, or said molecular weight is about 26,500 daltons.

5. The complex of claim 4, wherein said starch is selected from the group consisting of rice starch, corn starch, potato starch, and potato soluble starch.

6. A pharmaceutical composition comprising the complex of claim 1, and a pharmaceutically acceptable carrier.

7. The complex of claim 1, wherein said quaternized polysaccharide is quaternized to its full capacity.

8. The complex of claim 7, wherein said quaternized polysaccharide is quaternized starch having at least 3.5-4% nitrogen per monomeric unit, by weight.

9. A method for delivering a siRNA or miRNA to a target cell by administration of said siRNA or miRNA complexed with a quaternized polysaccharide, said polysaccharide being selected from the group consisting of starch, amylose, amylopectin, galactan and dextrin.

10. The method of claim 9, further comprising applying ultrasound to a subject prior to, at the same time, and/or following administering said siRNA or miRNA complexed with the quaternized polysaccharide.

11. The method of claim 9, wherein said quaternized polysaccharide is quaternized starch.

12. A method for treatment of ovarian cancer in a subject in need thereof, comprising administering to said subject a complex comprising siRNA or miRNA targeting the gene ABCB1 complexed with quaternized starch, wherein said ovarian cancer is amenable to treatment with said siRNA or miRNA.

\* \* \* \* \*

UNITED STATES PATENT AND TRADEMARK OFFICE
CERTIFICATE OF CORRECTION

PATENT NO. : 9,566,346 B2
APPLICATION NO. : 14/765790
DATED : February 14, 2017
INVENTOR(S) : Kost et al.

It is certified that error appears in the above-identified patent and that said Letters Patent is hereby corrected as shown below:

In the Specification

In Column 1 at Line 50, Change "both," to --both--.

In Column 4 at Line 35, Change "Lypiphilic" to --Lipophilic--.

In Column 6 at Line 19, After "Transfection" insert --.--.

In Column 7 at Line 58, Change "colacasia," to --colocasia,--.

In Column 12 at Line 2, Change "carbomethylcellulose;" to --carboxymethylcellulose;--.

In Column 16 at Line 5, Change "Brucker" to --Bruker--.

In Column 23 at Line 5, After "application" insert --.--.

In Column 25 at Line 33, Change "Lypiphilic" to --Lipophilic--.

In Column 26 at Line 21, After "transfection" insert --.--.

In Column 29 at Line 38, Change "Gudjons son" to --Gudjonsson--.

In Column 31 at Line 52 (approx.), Change "micralga" to --microalga--.

In Column 31 at Line 60 (approx.), Change "Brittish" to --British--.

Signed and Sealed this
Twenty-seventh Day of June, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,566,346 B2

In the Claims

In Column 32 at Line 63, In Claim 5, change "claim 4," to --claim 3,--.

```
SEQUENCE LISTING

<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: synthetic nucleotides

<400> SEQUENCE: 1
ugguuuacau gucgacuaa                                              19

<210> SEQ ID NO 2
<211> LENGTH: 19
<212> TYPE: RNA
<213> ORGANISM: Artificial Sequence
<220> FEATURE:
<223> OTHER INFORMATION: synthetic nucleotides

<400> SEQUENCE: 2
gaccauaaau guaagguuu                                              19
```